US009883844B2

(12) United States Patent
Kuwabara

(10) Patent No.: US 9,883,844 B2
(45) Date of Patent: Feb. 6, 2018

(54) BREAST THICKNESS MEASURING APPARATUS, BREAST THICKNESS MEASURING METHOD, AND RADIOGRAPHIC IMAGE CAPTURING SYSTEM

(71) Applicant: FUJIFILM Corporation, Tokyo (JP)

(72) Inventor: Takao Kuwabara, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 260 days.

(21) Appl. No.: 14/633,696

(22) Filed: Feb. 27, 2015

(65) Prior Publication Data
US 2015/0265186 A1    Sep. 24, 2015

(30) Foreign Application Priority Data

Mar. 19, 2014    (JP) .................................. 2014-056540

(51) Int. Cl.
*A61B 6/00*    (2006.01)
*A61B 6/02*    (2006.01)
(Continued)

(52) U.S. Cl.
CPC ............ *A61B 6/502* (2013.01); *A61B 5/1075* (2013.01); *A61B 5/708* (2013.01); *A61B 6/025* (2013.01);
(Continued)

(58) Field of Classification Search
CPC ..... A61B 6/0414; A61B 6/4233; A61B 6/502; A61B 6/542; A61B 6/544
(Continued)

(56) References Cited

U.S. PATENT DOCUMENTS 5,526,394 A * 6/1996 Siczek ................. A61B 6/4233
378/145
5,627,869 A * 5/1997 Andrew ................. A61B 6/502
378/150
(Continued)

FOREIGN PATENT DOCUMENTS

JP    2006-068506 A    3/2006
JP    2006-280444 A    10/2006
(Continued)

OTHER PUBLICATIONS

Japanese Notification of Reasons for Refusal dated Jan. 31, 2017, for Japanese Application No. 2014-056540, with an English translation.

*Primary Examiner* — Allen C. Ho
(74) *Attorney, Agent, or Firm* — Birch, Stewart, Kolasch & Birch, LLP

(57) ABSTRACT

A breast thickness measuring apparatus and a breast thickness measuring method are applied to a radiographic image capturing system. After a breast, which is placed on a support table, has been compressed by a compression plate having a marker disposed thereon, the breast is irradiated with radiation emitted from a radiation source. A radiographic image is generated on the basis of radiation that has passed through the breast, and a marker image, which is included within the radiographic image, is detected by a marker detector. Finally, the thickness of the compressed breast is calculated by a thickness calculator on the basis of a position of the detected marker image, a position of the radiation source, and information concerning the compression plate.

9 Claims, 12 Drawing Sheets

(51) Int. Cl.
*A61B 6/04* (2006.01)
*A61B 5/107* (2006.01)
*A61B 5/00* (2006.01)
*A61B 6/12* (2006.01)

(52) U.S. Cl.
CPC .............. *A61B 6/0414* (2013.01); *A61B 6/12* (2013.01); *A61B 6/4233* (2013.01); *A61B 6/5211* (2013.01); *A61B 6/542* (2013.01); *A61B 6/544* (2013.01)

(58) Field of Classification Search
USPC .......................................................... 378/37
See application file for complete search history.

(56) References Cited

U.S. PATENT DOCUMENTS

| | | | | |
|---|---|---|---|---|
| 6,041,094 | A * | 3/2000 | Russell | A61B 6/583 378/162 |
| 6,269,148 | B1 * | 7/2001 | Jessop | G01N 23/04 378/162 |
| 6,516,045 | B2 * | 2/2003 | Shepherd | A61B 6/502 378/132 |
| 7,092,482 | B2 * | 8/2006 | Besson | A61B 6/0414 378/37 |
| 7,286,632 | B2 * | 10/2007 | Yang | A61B 5/1075 378/164 |
| 7,443,950 | B2 * | 10/2008 | Sendai | A61B 6/0414 378/195 |
| 7,453,979 | B2 * | 11/2008 | Sendai | A61B 6/025 378/23 |
| 7,545,908 | B2 * | 6/2009 | Hemmendorff | A61B 6/502 378/205 |
| 7,613,276 | B2 * | 11/2009 | Sendai | A61B 6/0414 378/37 |
| 7,734,013 | B2 * | 6/2010 | Kashiwagi | A61B 6/502 378/108 |
| 7,742,561 | B2 * | 6/2010 | Ueki | A61B 5/0091 378/37 |
| 7,746,975 | B2 * | 6/2010 | Kashiwagi | A61B 6/502 378/37 |
| 7,787,587 | B2 * | 8/2010 | Tasaki | A61B 6/502 378/108 |
| 8,465,204 | B2 * | 6/2013 | Kamiya | A61B 10/0275 378/204 |
| 8,467,495 | B2 * | 6/2013 | Okada | A61B 6/022 378/151 |
| 8,768,026 | B2 * | 7/2014 | Ren | A61B 6/0414 382/131 |
| 8,838,207 | B2 * | 9/2014 | Nakayama | A61B 6/0414 378/147 |
| 8,848,865 | B2 * | 9/2014 | Nakayama | A61B 6/0414 378/37 |
| 8,938,087 | B2 * | 1/2015 | Han | G06T 5/50 382/100 |
| 9,008,382 | B2 * | 4/2015 | Highnam | G06T 7/0012 382/128 |
| 9,098,935 | B2 * | 8/2015 | Endo | A61B 6/463 |
| 9,526,471 | B2 * | 12/2016 | Goodenough | A61B 6/583 |
| 9,532,752 | B2 * | 1/2017 | Goossen | A61B 6/0414 |
| 9,675,277 | B2 * | 6/2017 | Arai | A61B 5/1075 |
| 2006/0029268 | A1 | 2/2006 | Endo et al. | |
| 2006/0167355 | A1 * | 7/2006 | Rico | A61B 6/502 600/407 |
| 2016/0029979 | A1 * | 2/2016 | Mawdsley | A61B 6/0414 378/37 |

FOREIGN PATENT DOCUMENTS

JP          2010-183965 A    8/2010
WO     WO 2013/035023 A     3/2013

* cited by examiner

BREAST THICKNESS MEASURING APPARATUS, BREAST THICKNESS MEASURING METHOD, AND RADIOGRAPHIC IMAGE CAPTURING SYSTEM

CROSS-REFERENCE TO RELATED APPLICATION

This application is based upon and claims the benefit of priority from Japanese Patent Application No. 2014-056540 filed on Mar. 19, 2014, the contents of which are incorporated herein by reference.

BACKGROUND OF THE INVENTION

Field of the Invention

The present invention relates to a breast thickness measuring apparatus and a breast thickness measuring method for measuring the thickness of a breast, which is compressed between a compression plate and a support table. The present invention also concerns a radiographic image capturing system for capturing a radiographic image of a breast.

Description of the Related Art

Heretofore, it has been customary to capture a radiographic image of a breast of a subject with a mammographic apparatus, by placing the breast on a support table, compressing the breast with a compression plate, irradiating the breast with radiation emitted from a radiation source, and generating a radiographic image of the breast with a radiographic image generator on the basis of radiation that has passed through the breast.

Japanese Laid-Open Patent Publication No. 2010-183965 discloses that in order to acquire a good radiographic image, a compression plate is marked with a marker, and a positional deviation of a radiation source from a normal position (proper focused position) with respect to a radiographic image generator is calculated on the basis of the position of a marker image, which is included in a radiographic image, thereby allowing the position of the radiation source to be adjusted to the focused position. Japanese Laid-Open Patent Publication No. 2006-280444 reveals that the spacing between upper and lower compression plates between which the breast is compressed, i.e., the thickness of the breast that is compressed between the upper and lower compression plates, is calculated from a plurality of tomosynthetically produced sliced images.

SUMMARY OF THE INVENTION

For acquiring a satisfactory radiographic image of a compressed breast, it is desirable to make an accurate measurement of the thickness of the compressed breast, i.e., the height of a compression plate from a support table at a time that the compression plate compresses the breast against the support table, and to set image capturing conditions under which a radiographic image of the compressed breast is captured.

The technology disclosed in Japanese Laid-Open Patent Publication No. 2010-183965 is concerned with adjusting the focused position of the radiation source, but is not concerned with measuring the height of the compression plate. Further, according to the technology disclosed in Japanese Laid-Open Patent publication No. 2006-280444, the subject is exposed to an undue amount (dose) of radiation due to the fact that the thickness of the breast, which is calculated from the tomosynthetically produced sliced images, requires a plurality of irradiation events, resulting in a high dose of radiation.

An object of the present invention is to provide a breast thickness measuring apparatus and a breast thickness measuring method for accurately measuring the thickness of a breast, which is compressed by a compression plate, on the basis of a single radiographic image produced by a single radiographic image capturing process that is performed on the compressed breast. A further object of the present invention is to provide a radiographic image capturing system for capturing a radiographic image of the breast.

According to the present invention, a breast thickness measuring apparatus includes a support table on which a breast of a subject is placed, a compression plate configured to compress the breast, which is placed on the support table, a radiation source configured to apply radiation in a prescribed direction to the breast, which is compressed by the compression plate, and a radiographic image generator configured to generate a radiographic image on the basis of radiation that has passed through the breast.

To achieve the above object, the breast thickness measuring apparatus further includes a marker disposed on the compression plate, a marker detector configured to detect from the radiographic image a marker image representing the marker included within the radiographic image, and a thickness calculator configured to calculate the thickness of the compressed breast from a position of the detected marker image, a position of the radiation source, and information concerning the compression plate.

A breast thickness measuring method according to the present invention includes the following first through fifth steps.

In the first step, a compression plate having a marker disposed thereon compresses a breast of a subject that is placed on a support table. In the second step, a radiation source applies radiation in a prescribed direction to the breast, which is compressed by the compression plate. In the third step, a radiographic image generator generates a radiographic image on the basis of radiation that has passed through the breast. In the fourth step, a marker detector detects, from the radiographic image, a marker image representing the marker included within the radiographic image. In the fifth step, a thickness calculator calculates the thickness of the compressed breast from a position of the detected marker image, a position of the radiation source, and information concerning the compression plate.

A radiographic image capturing system according to the present invention includes the support table, the compression plate, the marker, the radiation source, the radiographic image generator, the marker detector, and the thickness calculator, which have been described above. In addition, the radiographic image capturing system has a display unit.

According to the present invention, in a case where a single radiographic image is produced by a single radiographic image capturing process performed on the breast, which is compressed by the compression plate, the marker image that is included within the single radiographic image is detected, and the thickness of the compressed breast is calculated on the basis of the position of the detected marker image, the position of the radiation source, and information concerning the compression plate. Therefore, the thickness of the compressed breast can be calculated without the need for a plurality of radiographic image capturing processes being performed on the breast, as required in Japanese Laid-Open Patent Publication No. 2006-280444. Thus, the thickness of the compressed breast can accurately be determined without having the subject exposed to an unduly high dose of radiation.

Image capturing conditions for a main image capturing process are set on the basis of the thickness of the breast that is obtained by such a pre-irradiating process. Thereafter, a radiographic image capturing process (main image capturing process) is performed on the compressed breast according to the image capturing conditions, which have been set. As a result, a radiographic image of the compressed breast, which is of good image quality, can reliably be acquired.

The breast thickness measuring apparatus may further include a compression plate position detector configured to detect a position of the compression plate, and a compression plate size acquirer configured to acquire a size of the compression plate. The thickness calculator may calculate the thickness of the breast, which is compressed, on the basis of the position of the detected marker image, the position of the radiation source, the position of the compression plate, which compresses the breast, and the size of the compression plate. Accordingly, the thickness of the compressed breast can be calculated with high accuracy using the position and the size of the compression plate, as represented by the information concerning the compression plate.

More specifically, the breast thickness measuring apparatus may calculate the thickness of the compressed breast in the following manner.

The radiographic image generator may generate a first radiographic image on the basis of radiation, which is applied from the radiation source through the compression plate while the compression plate is held in contact with the support table, and may generate a second radiographic image on the basis of radiation, which is applied from the radiation source through the compression plate and has passed through the breast while the compression plate compresses the breast.

The marker detector may detect a first marker image, which is included in the first radiographic image, and a second marker image, which is included in the second radiographic image.

The thickness calculator may calculate the position of the marker on the compression plate, which compresses the breast, on the basis of the position of the first marker image, the position of the second marker image, and the position of the radiation source. Then, the thickness calculator may calculate the distance by which the compression plate, which compresses the breast, is tilted, on the basis of the calculated position of the marker, the calculated position of the first marker image, the position of the compression plate, which compresses the breast, and the size of the compression plate. Finally, the thickness calculator may calculate the thickness of the breast, which is compressed, on the basis of the position of the compression plate, which compresses the breast, and the calculated distance by which the compression plate, which compresses the breast, is tilted.

The first radiographic image is an image generated in a case where radiation is applied while the compression plate is held in contact with the support table with the breast not being present therebetween. Consequently, only the first marker image is detected from the first radiographic image. On the other hand, the second radiographic image is an image generated in a case where radiation is applied while the breast is compressed between the compression plate and the support table. Consequently, a breast image representing the breast and the second marker image are detected from the second radiographic image.

Thus, the thickness calculator can calculate the position of the marker on the compression plate, which compresses the breast, from the position of the first marker image and the position of the second marker image, etc., and can calculate the distance by which the compression plate, which compresses the breast, is tilted from the position of the marker based on the position of the marker and the position of the compression plate that compresses the breast, etc. Accordingly, even though the compression plate undergoes flexure due to the shape of the breast in a case where the breast is pressed flatwise against the support table, the distance by which the compression plate is tilted can accurately be calculated while taking into account the flexure of the compression plate.

Therefore, even though the tilted compression plate compresses the breast, the thickness calculator accurately calculates the thickness of the compressed breast on the basis of the position of the compression plate and the distance by which the compression plate is tilted.

The marker may be disposed in a position spaced a prescribed distance from a side surface of the compression plate, the side surface closest to a chest wall of the subject. Thus, the marker, which is positioned in the foregoing manner, prevents the marker image from being included in the breast image.

In case that plural markers are provided, which are positioned one on each side of a central line of the compression plate, the marker detector detects marker images representing the respective markers included within the radiographic image. In addition, the thickness calculator calculates an angle through which the compression plate, which compresses the breast, is tilted laterally, on the basis of respective positions of the detected marker images, and calculates the thickness of the breast, which is compressed, on the basis of the calculated angle through which the compression plate, which compresses the breast, is tilted laterally, the positions of the marker images, the position of the radiation source, and the information concerning the compression plate. Therefore, even in case that the compression plate is tilted laterally with respect to the support table in a case where the compression plate compresses the breast, the thickness calculator can suitably calculate the thickness of the compressed breast.

The above and other objects, features, and advantages of the present invention will become more apparent from the following description in a case where taken in conjunction with the accompanying drawings, in which preferred embodiments of the present invention are shown by way of illustrative example.

DESCRIPTION OF THE PREFERRED EMBODIMENTS

Figure 1:
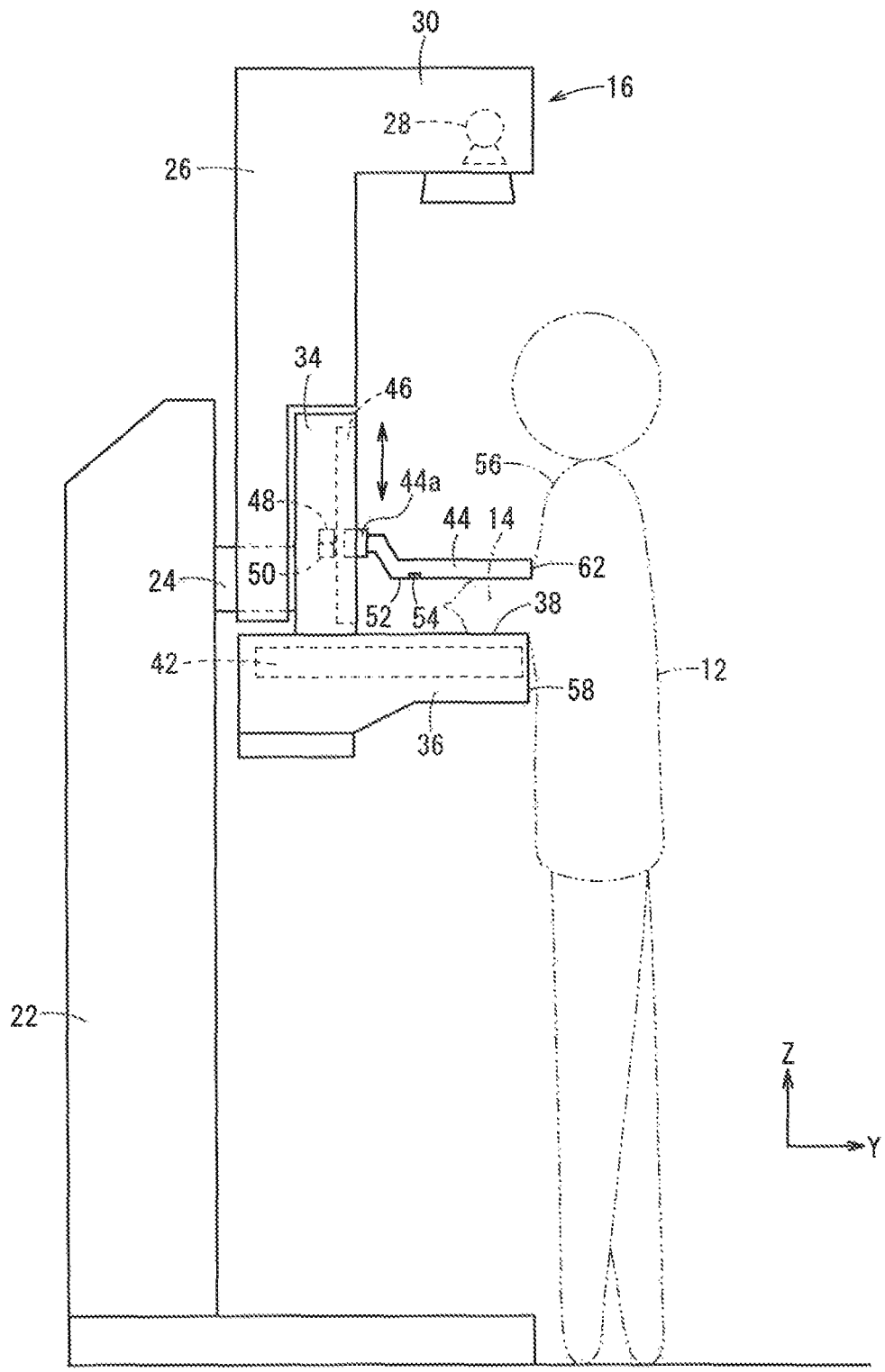
FIG. 1 is a side elevational view of a radiographic image capturing apparatus, which is incorporated in a breast thickness measuring apparatus according to an embodiment of the present invention.

Like or corresponding parts are denoted by like or corresponding reference characters throughout the views.

A breast thickness measuring apparatus according to a preferred embodiment of the present invention will be described in detail below with reference to the accompanying drawings, in relation to a breast thickness measuring method carried out by such a breast thickness measuring apparatus.

Arrangement of Breast Thickness Measuring Apparatus

As shown in FIGS. 1 through 4, a breast thickness measuring apparatus 10 according to an embodiment of the present invention is applied to a radiographic image capturing system 20, which includes a radiographic image capturing apparatus 16 as a mammographic apparatus for capturing a radiographic image of a breast 14 of a subject 12, and a console 18 for controlling the radiographic image capturing apparatus 16. The radiographic image capturing apparatus 16 is used in a radiological department of a medical organization, which for example, may be a hospital.

Figure 2:
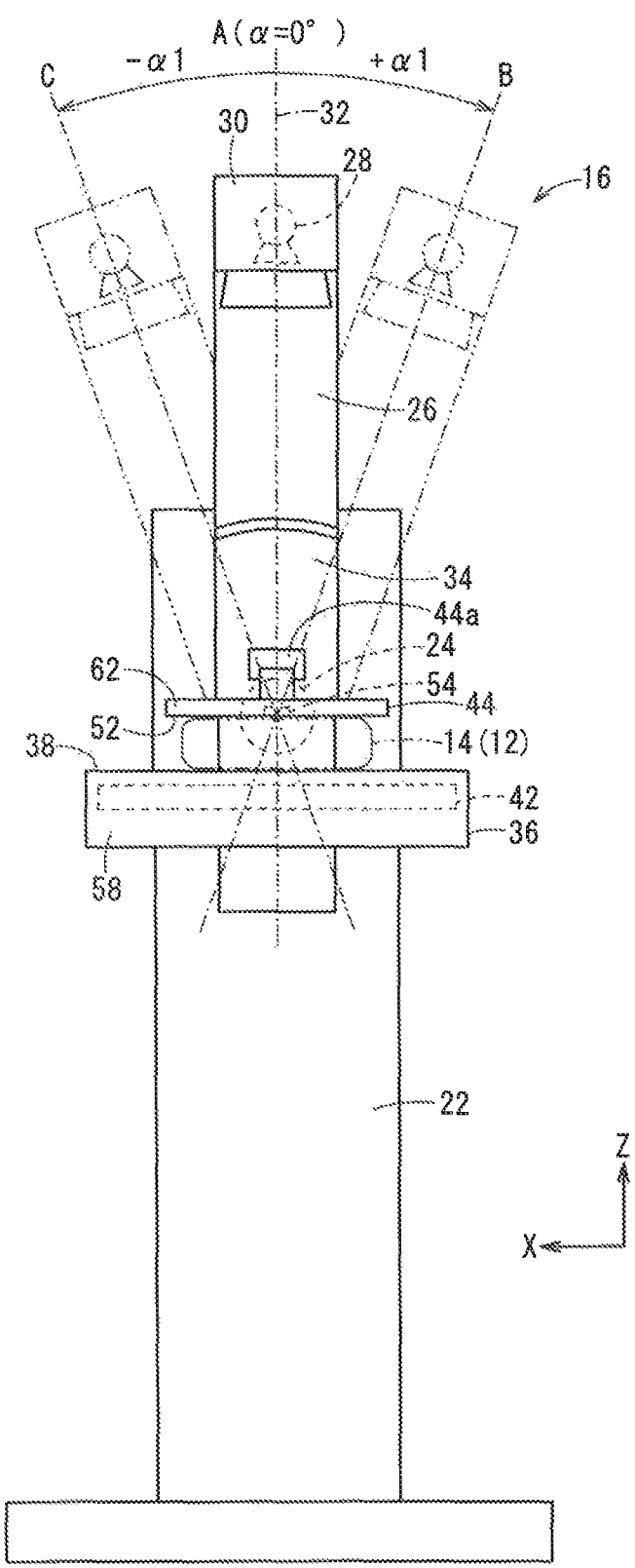
FIG. 2 is a front elevational view of the radiographic image capturing apparatus shown in FIG. 1.

As shown in FIGS. 1 and 2, the radiographic image capturing apparatus 16 has an upright base 22 with a rotatable shaft 24 mounted on an upper portion of a side surface of the base 22 that faces toward a subject 12 to be imaged by the radiographic image capturing apparatus 16. The rotatable shaft 24, which is rotatable about a horizontal axis, extends axially in the direction of the arrow Y. An arm 26 is fixed to the rotatable shaft 24.

The rotatable shaft 24 supports the arm 26, the upper distal end of which is constructed as a radiation source housing 30 in which a radiation source 28 is accommodated. In a case where the rotatable shaft 24 turns about a horizontal axis thereof, the arm 26, the radiation source 28, and the radiation source housing 30 turn in unison with each other within a predetermined angular range from $-\alpha 1$ to $+\alpha 1$, for example, across a central angle ($\alpha=0°$), which is aligned with a vertical axis 32 that extends vertically through the horizontal axis of the rotatable shaft 24 in the direction of the arrow Z.

The position of the radiation source 28 at $\alpha=0°$ will be referred to as position A, the position of the radiation source 28 at $\alpha=+\alpha 1°$ will be referred to as position B, and the position of the radiation source 28 at $\alpha=-\alpha 1°$ will be referred to as position C. Unless otherwise noted, it is assumed that in position A, the radiation source 28 emits radiation 40 (see FIG. 4) along the vertical axis 32 in the direction of the arrow Z, as a prescribed direction toward an image capturing table (support table) 36.

A holder 34 is coupled to the distal end of the rotatable shaft 24. The image capturing table 36 on which the breast 14 of the subject 12 is placed is mounted on a lower end of the holder 34. The image capturing table 36 has an upper rest surface 38 on which the breast 14 is placed. At least the rest surface 38 of the image capturing table 36 is made of a material that is permeable to radiation 40. The image capturing table 36 houses a planar radiation detector 42 in the form of a flat panel detector (FPD) for converting radiation 40 emitted from the radiation source 28 into a radiographic image.

The radiation detector 42 is either a direct-conversion radiation detector for directly converting radiation 40 into electric signals, or an indirect-conversion radiation detector for converting radiation 40 into light in a prescribed wavelength range with a scintillator, and then converting the light into electric signals. The radiation detector 42 includes a matrix of pixels arranged in rows and columns for converting radiation 40 into electric signals and storing the signals as electric charges. Each of the pixels has a thin-film transistor (TFT) that serves as a switching device. In a case where the TFTs of one row are turned on simultaneously, electric charges stored in the corresponding pixels are read out and amplified by amplifiers. The amplified electric charges are transmitted through a multiplexer to an A/D converter, which converts the electric charges into digital signals. Each of the TFTs may be combined with another image capturing device, such as a complementary metal-oxide semiconductor (CMOS) image sensor or the like.

A compression plate 44, which is made of a material permeable to radiation 40, is mounted on the holder 34. A proximal end 44a of the compression plate 44 is inserted in a compression plate moving mechanism 46, which includes a vertical rail disposed in the holder 34. The compression plate 44 can be displaced vertically along the direction of the arrow Z by the compression plate moving mechanism 46.

The holder 34 houses a compression plate position detector 48 and a compression plate size detector (compression plate size acquirer) 50, which are positioned in the vicinity of the compression plate moving mechanism 46.

The compression plate position detector 48 is a position detecting sensor for detecting a vertical position or height of the proximal end 44a, so as to detect the vertical position of a compression surface 52, which is represented by the bottom surface of the compression plate 44, with respect to the rest surface 38 or the radiation detector 42. More specifically, the compression plate position detector 48 is embedded in the holder 34 in the vicinity of the position where the proximal end 44a is inserted in the compression plate moving mechanism 46, or alternatively, the compression plate position detector 48 is embedded in the proximal end 44a. Therefore, the compression plate position detector 48 can detect the vertical position of (the compression surface 52) of the compression plate 44 on the basis of the vertical position of the proximal end 44a along the direction of the arrow Z in the compression plate moving mechanism 46.

Figure 7:
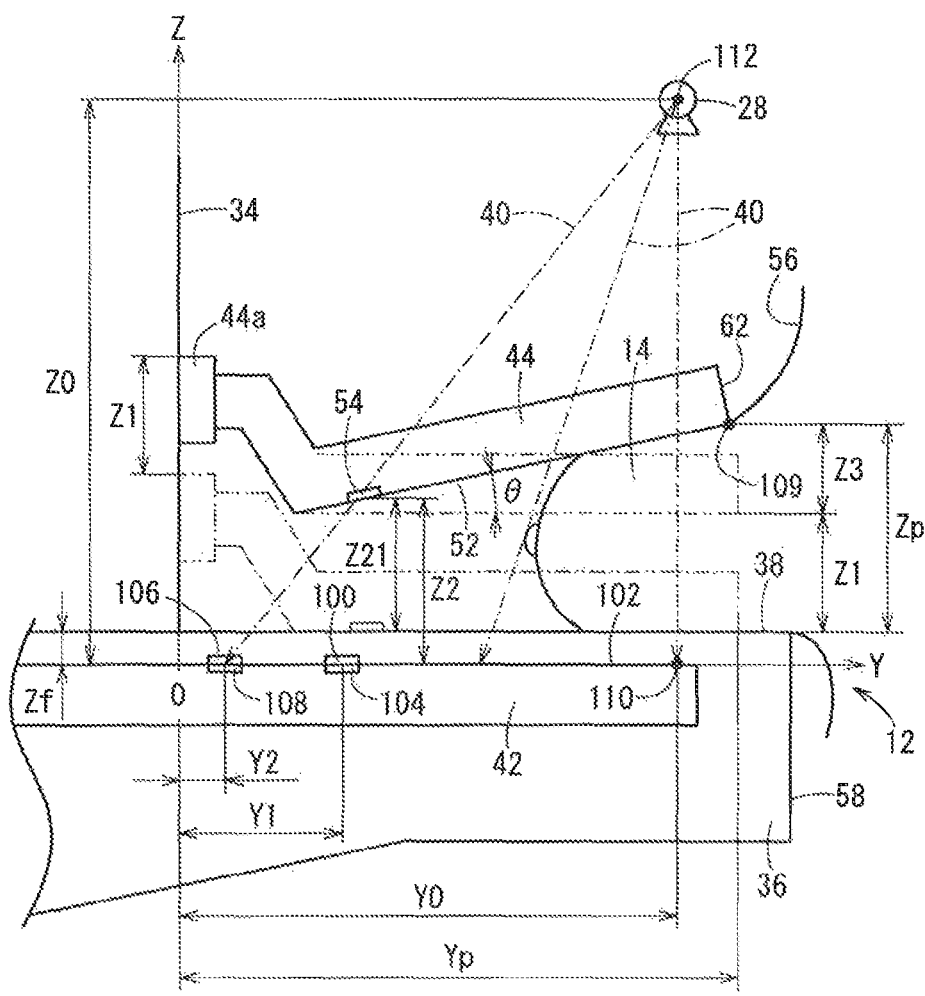
FIG. 7 is a schematic view illustrating a breast image capturing process (pre-irradiating process)

According to the present embodiment, as shown in FIG. 7, for example, a relative position (relative height) of the compression surface 52 with respect to the rest surface 38 at the time that the compression plate 44 is lifted in the direction of the arrow Z from a reference surface, which is represented by the rest surface 38, is referred to as a height Z1 of the compression surface 52 of the compression plate 44. However, the present embodiment is not strictly limited to the above definition for the height Z1. Alternatively, the relative position of the compression surface 52 with respect to a reference surface, which is represented by a detection surface 102 of the radiation detector 42, may be defined as the height Z1 of the compression surface 52 of the compression plate 44.

The compression plate size detector 50 acquires the size, type, and model number of the compression plate 44, and the position of a marker 54 on the compression plate 44, etc., by reading a set of convexities and concavities provided on the proximal end 44a, or by reading a bar code applied to the proximal end 44a, at the time that the proximal end 44a is inserted into the compression plate moving mechanism 46.

More specifically, assuming there are a plurality of compression plates 44 having proximal ends 44a that can be inserted selectively into the compression plate moving mechanism 46, then sets of convexities and concavities in different shapes, numbers, and positions are given respectively to the compression plates 44. In a case where the proximal end 44a of a selected one of the compression plates 44 is inserted into the compression plate moving mechanism 46, the compression plate size detector 50 can identify the size, type, and model number of the compression plate 44, as well as the position of the marker 54 on the compression plate 44, etc., from the set of convexities and concavities on the inserted proximal end 44a.

On the other hand, assuming that different bar codes are applied respectively to the proximal end 44a, then in case that the proximal end 44a of a selected one of the compression plates 44 is inserted into the compression plate moving mechanism 46, the compression plate size detector 50 can identify the size, type, and model number of the compression plate 44, as well as the position of the marker 54 on the compression plate 44, etc., which are represented by the bar code, by reading the bar code on the inserted proximal end 44a.

Figure 6:
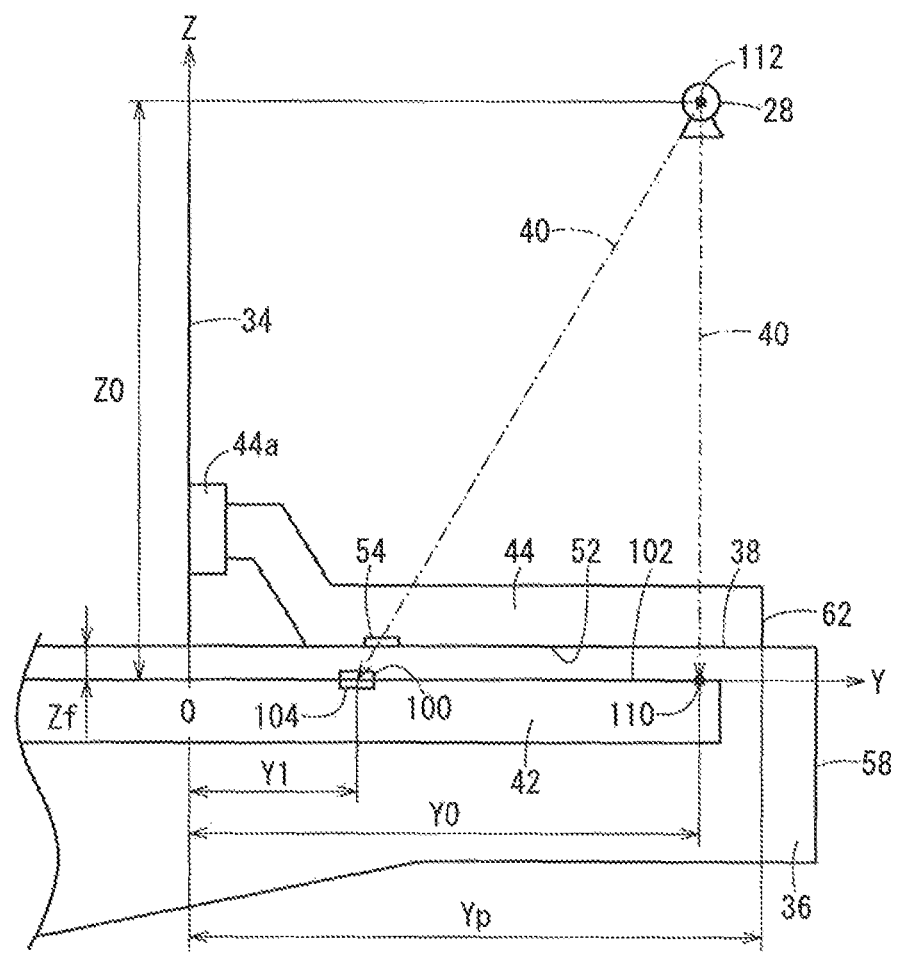
FIG. 6 is a schematic view illustrating a calibration image capturing process.

As shown in FIG. 6, the size of the compression plate 44 includes a distance Yp along the direction of the arrow Y from a side surface (origin O of a Y-axis and a Z-axis) of the holder 34 to a distal-end side surface 62 of the compression plate 44. According to the present embodiment, the compression plate size detector 50 may detect at least the distance Yp, which represents size information in a depthwise direction of the compression plate 44.

The holder 34, the image capturing table 36, the radiation detector 42, and the compression plate 44 are disposed bilaterally and symmetrically with respect to the vertical axis 32 along the direction of the arrow X.

The breast 14 of the subject 12 is compressed in the following manner by the compression plate 44. The subject 12 stands near the image capturing table 36 while keeping the chest wall 56 of the subject 12 in contact with a distal-end side surface 58 of the image capturing table 36, with the breast 14 of the subject 12 being placed on the rest surface 38. In this state, the compression plate moving mechanism 46 is actuated in order to lower the compression plate 44 toward the image capturing table 36 until the breast 14 is compressed between the compression surface 52 of the compression plate 44 and the rest surface 38 of the image capturing table 36. As described later, in a case where the breast 14 is compressed by the compression plate 44, a portion of the compression plate 44 near the chest wall 56 may be subjected to flexure due to the shape of the breast 14 that is placed on the rest surface 38. In FIGS. 1 and 2, the compression plate 44 is illustrated before the compression plate 44 is flexed.

The rotatable shaft 24 and the holder 34 include non-illustrated intermeshing gears disposed therein. The intermeshing state of the gears can be adjusted such that the holder 34 is either in a first mode of operation, in which the holder 34 is operatively connected to the rotatable shaft 24 for rotation in unison therewith, or in a second mode of operation, in which the holder 34 is operatively disconnected from the rotatable shaft 24 to undergo idle rotation.

For example, for capturing a craniocaudal (CC) mammogram as a radiographic image of the breast 14, the holder 34 is kept in the second mode of operation, so as to undergo idle rotation with respect to the rotatable shaft 24, and the radiation source 28 is placed in position A, as shown in FIG. 2. In this state, the radiation source 28 is energized to emit radiation 40 along the vertical axis 32 toward the breast 14, which is compressed between the compression plate 44 and the image capturing table 36.

On the other hand, for capturing a mediolateral oblique (MLO) mammogram as a radiographic image of the breast 14, the holder 34 is kept in the first mode of operation, so as to rotate in unison with the rotatable shaft 24. In this state, the arm 26, the holder 34, and the image capturing table 36 are turned in unison with each other. The breast 14 is obliquely compressed between the compression plate 44 and the image capturing table 36, and the radiation source 28 is energized to emit radiation 40 toward the compressed breast 14.

In the following description, it is assumed that the holder 34 is kept in the second mode of operation, so as to undergo idle rotation with respect to the rotatable shaft 24, whereas the rest surface 38 of the image capturing table 36 lies horizontally along the direction of the arrow X and the direction of the arrow Y.

Figure 3:
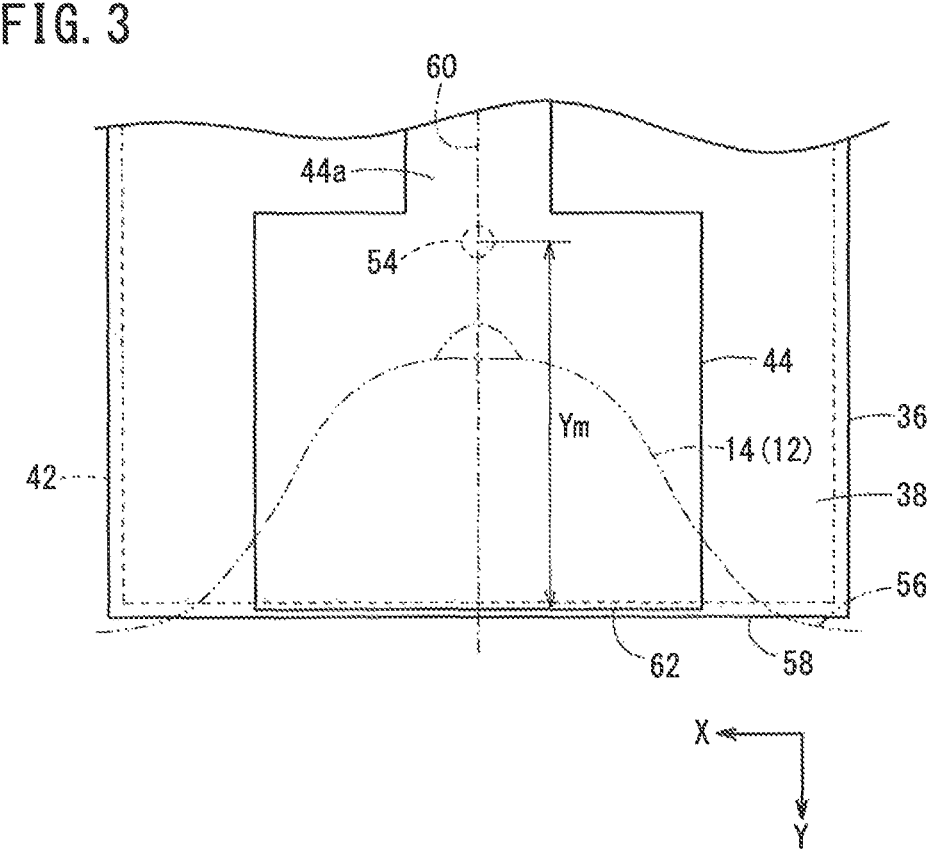
FIG. 3 is a plan view of a compression plate and a support table of the radiographic image capturing apparatus shown in FIG. 1.

According to the present embodiment, the marker 54 preferably is placed in a position that is spaced a prescribed distance from the distal-end side surface 62 of the compression plate 44 that faces toward the chest wall 56 of the subject 12. In FIG. 3, the marker 54 is embedded in the compression plate 44 at a position on a central line 60, which extends along the direction of the arrow Y and through a central position of the compression plate 44 with respect to the direction of the arrow X. The position of the marker 54 is spaced a prescribed distance Ym from the distal-end side surface 62 that is kept in contact with the chest wall 56. The marker 54 is embedded in the compression plate 44 such that the lower surface thereof lies substantially flush with the compression surface 52 of the compression plate 44. Thus, the marker 54, which is spaced by the distance Ym, is spaced from the breast 14 that is compressed. Therefore, as described later, the distance Ym is set such that, in a case where the radiation source 28 applies radiation 40 to the compressed breast 14, and the radiation detector 42 converts radiation 40 that has passed through the breast 14 into a radiographic image, the radiographic image does not include an image (marker image) of the marker 54 within the image (breast image) of the breast 14.

According to the present embodiment, furthermore, the marker 54 preferably is positioned on an X-Y plane, i.e., a plane defined by an X-axis represented by the direction of the arrow X, and a Y-axis represented by the direction of the arrow Y. The marker 54 is positioned more deeply, i.e., more closely to the proximal end 44a of the compression plate 44, than a central position of the compression plate 44 with respect to the direction of the arrow Y. More preferably, the marker 54 is positioned on the X-Y plane at a position that lies within about 10% of the distance from a side near the holder 34 (i.e., a deeper side) of a rectangular shape representing the compression plate 44 along the depth of the compression plate 44 in the direction of the arrow Y. With the marker 54 positioned in this manner, in a case where a breast 14, which may be of any potential size, is compressed, the marker 54 is spaced from the breast 14. Further, in a case where a radiographic image of the compressed breast 14 is captured, the marker image is included within the radiographic image at a position that is spaced from the breast image. Therefore, using a marker detector 94, to be described later, the marker image can easily be detected from the radiographic image.

The marker 54 preferably is made of a material that can absorb radiation 40, or stated otherwise, a material impermeable to radiation 40, such as copper, lead, platinum, gold, tantalum alloy, alumina, etc. The marker 54 may be of any shape that can be distinguished visually from a calcified area, spicule, mass, or the like in the breast 14. For example, the marker 54 may be of a circular shape, a ring shape, a crisscross shape, or a heart shape as viewed in plan.

Figure 4:
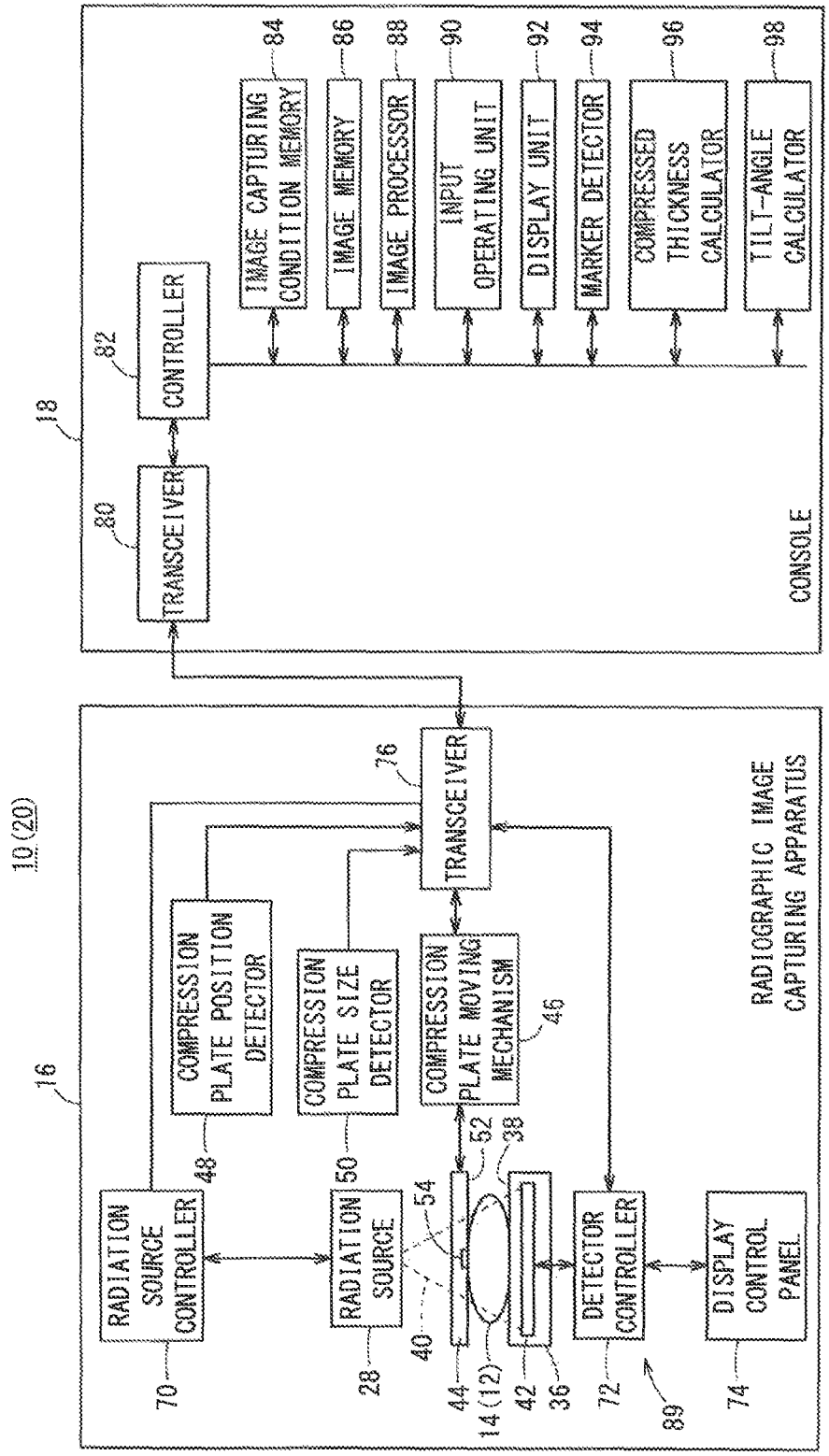
FIG. 4 is a block diagram of the breast thickness measuring apparatus according to the embodiment.

As shown in FIG. 4, the radiographic image capturing system 20 to which the breast thickness measuring apparatus 10 according to the present embodiment is applied includes the radiographic image capturing apparatus 16 and the console 18, as described above.

In addition to the components shown in FIGS. 1 through 3, the radiographic image capturing apparatus 16 includes a radiation source controller 70, a detector controller 72, a display control panel 74, and a transceiver (signal transmitting/receiving unit) 76. The radiation source controller 70 controls the radiation source 28 according to image capturing conditions that are sent from the console 18 through the transceiver 76 to the radiation source controller 70. The detector controller 72 controls the radiation detector 42 according to the image capturing conditions in order to detect a radiographic image, acquires the detected radiographic image from the radiation detector 42, and transmits the acquired radiographic image through the transceiver 76 to the console 18. The display control panel 74 displays image capturing information representing a region to be imaged of the subject 12, an imaging direction, etc., together with ID information, etc., of the subject 12. In addition, in case that necessary, the display control panel 74 is capable of establishing the image capturing information and the ID information. The transceiver 76 operates to send signals to and receive signals from the console 18.

The image capturing conditions refer to conditions representing a tube voltage, an mAs value, etc., which specify the dose of radiation 40 to be applied to the breast 14. The image capturing conditions are set in the radiation source controller 70 in the event that radiographic image capturing processes (a pre-irradiating process and a main image capturing process) are performed on the breast 14.

The console 18, which is installed in a treatment room adjacent to an image capturing room of a radiological department, serves to manage and control the radiographic image capturing apparatus 16. The console 18 is connected, through an in-house network, to a hospital information system (HIS) for managing medical processing procedures in the hospital, a radiological information system (RIS) for managing radiographic image capturing processes under the control of the HIS, and a viewer that is used by the doctor to interpret and diagnose captured radiographic images.

More specifically, the console 18 includes a transceiver 80 for sending signals to and receiving signals from the radiographic image capturing apparatus 16, as well as for sending signals to and receiving signals from the viewer, the HIS, and the RIS through the in-house network. The console 18 further includes a controller 82 for controlling components of the radiographic image capturing apparatus 16 and the console 18. In the console 18, the controller 82 is connected to an image capturing condition memory 84, an image memory 86, an image processor 88, an input operating unit (compression plate size acquirer) 90, a display unit 92, a marker detector 94, a compressed thickness calculator (thickness calculator) 96, and a tilt-angle calculator 98.

The image capturing condition memory 84 stores image capturing conditions, which are set by a radiologist that operates the input operating unit 90. For performing a radiographic image capturing process on the breast 14, the controller 82 is capable of setting the image capturing conditions in the radiation source controller 70 via the transceivers 76, 80.

The image memory 86 stores a radiographic image that is acquired from the radiographic image capturing apparatus 16. Since the breast 14 and the marker 54, which is capable of absorbing radiation 40, are located within a range that is irradiated with radiation 40, a radiographic image, which is captured in a case where a radiographic image capturing process is performed on the breast 14, includes an image of the breast 14 (breast image) together with an image of the marker 54 (marker image).

The image processor 88 performs a prescribed image processing sequence on a radiographic image that is stored in the image memory 86. The radiation detector 42, the detector controller 72, and the image processor 88 jointly make up a radiographic image generator 89 that generates an image, which is projected as a radiographic image onto the radiation detector 42 (projected image) in a radiographic image capturing process. The radiographic image generator 89 may alternatively be composed of the radiation detector 42, the detector controller 72, and signal processing software that is installed in the console 18, insofar as the radiographic image generator 89 is capable of generating a radiographic image as a projected image. The image processor 88 also includes a marker removing function for removing the marker image, in order to generate a radiographic image of the breast 14 that is free of the image of the marker 54. Such a marker removing function can be performed by an interpolating process, which interpolates the data made up of pixels of the marker image with the data of pixels that are positioned around the marker image.

The input operating unit 90 receives input actions that are taken by the radiologist. By operating the input operating unit 90, the radiologist can enter, in addition to image capturing conditions, the size of the compression plate 44, e.g., the distance Yp across the depth of the compression plate 44. The controller 82 can store the entered size of the compression plate 44, as well as the image capturing conditions, in the image capturing condition memory 84.

The display unit 92 is capable of displaying various pieces of information, including a radiographic image that is processed by the image processor 88. In particular, as will be described later, the display unit 92 is capable of simultaneously displaying the radiographic image and the thickness (compressed thickness) of the breast.

The marker detector 94 detects the image of the marker 54 (marker image) included within a radiographic image that is stored in the image memory 86, and identifies the position of the marker image in the radiographic image, i.e., the positions of the pixels where the marker image is detected by the radiation detector 42.

The compressed thickness calculator 96 calculates the thickness of the compressed breast 14 (breast thickness) in a case where the radiographic image of the breast 14 is captured, on the basis of the position of the marker image in the radiographic image detected by the marker detector 94, the position of the radiation source 28 at the time that the radiographic image is captured, the vertical position of the compression plate 44 (height Z1) detected by the compression plate position detector 48, and the size of the compression plate 44, etc.

In case that plural markers 54 are provided on the compression plate 44, as described later, the tilt-angle calculator 98 calculates a tilt angle of the compression plate 44, which compresses the breast 14, on the basis of the vertical positions of the markers 54, etc. In this case, the compressed thickness calculator 96 calculates the thickness of the compressed breast 14 also in view of the tilt angle calculated by the tilt-angle calculator 98.

The tilt-angle calculator 98 may be included in the console 18 only in case that necessary, and is not considered to be an indispensable component. Since the compressed thickness calculator 96 calculates the thickness of the compressed breast 14 also in view of the tilt angle, the function of the tilt-angle calculator 98 may be included in the compressed thickness calculator 96.

The compressed thickness calculator 96 calculates the thickness of the compressed breast 14 on the basis of the position of the marker image in the radiographic image, which is detected by the marker detector 94. Therefore, the compressed thickness calculator 96 may include the function of the marker detector 94.

In case that the radiologist operates the input operating unit 90 in order to enter the size, etc., of the compression plate 44, the compression plate size detector 50 may be dispensed with.

Operations of Breast Thickness Measuring Apparatus (Breast Thickness Measuring Method)

The breast thickness measuring apparatus 10 according to the present embodiment is constituted as described above. Operations of the breast thickness measuring apparatus 10 (breast thickness measuring method) will be described below with reference to FIGS. 5 through 10C, as well as FIGS. 1 through 4 as necessary.

According to a sequence to be described below, which is represented by the flowchart shown in FIG. 5 and is given as an example of a breast thickness measurement, first, the compression surface 52 is brought into contact with the rest surface 38 before the breast 14 is compressed by the compression plate 44. Next, a radiographic image capturing process (calibration image capturing process) is carried out, after which the breast 14 is compressed by the compression plate 44. Then, a radiographic image capturing process (breast image capturing process) in the form of a pre-irradiating process is carried out. Thereafter, the thickness of the compressed breast 14 (compressed thickness Zp) is determined on the basis of radiographic images captured by the calibration image capturing process and the breast image capturing process. Accordingly, in the case that the compressed thickness Zp is determined according to the flowchart shown in FIG. 5, the radiographic image capturing system 20 can set image capturing conditions for a main image capturing process, which is performed on the compressed breast 14 on the basis of the compressed thickness Zp.

Figure 5:
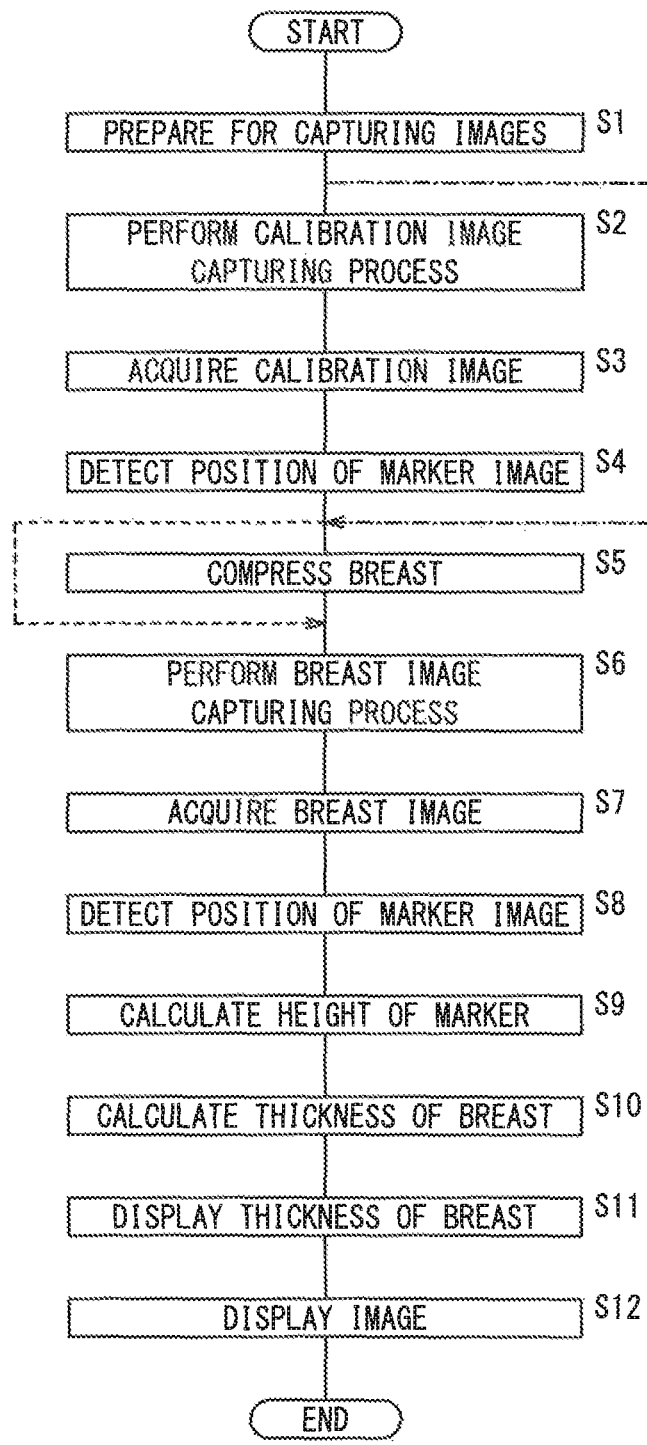
FIG. 5 is a flowchart of an operation sequence of the breast thickness measuring apparatus shown in FIG. 4.

In step S1 of FIG. 5, the radiologist operates the input operating unit 90 (see FIG. 4) of the console 18 in order to set ID information of the subject 12, an image capturing method for the breast 14, and image capturing conditions. The ID information, the image capturing method, and the image capturing conditions, which have been set, are stored in the image capturing condition memory 84. The ID information refers to information for identifying the subject 12, such as the name, age, etc., of the subject 12.

The radiologist selects one of the available compression plates 44, and inserts the proximal end 44a of the selected compression plate 44 into the compression plate moving mechanism 46. The compression plate size detector 50 recognizes the set of convexities and concavities that are provided on the inserted proximal end 44a, or alternatively, reads a bar code that is applied to the inserted proximal end 44a, thereby acquiring information concerning the compression plate 44, such as the size, type, and model number of the compression plate 44, the position of the marker 54 on the compression plate 44, etc. The acquired information concerning the compression plate 44 is sent through the transceivers 76, 80 to the console 18, and the acquired information is stored in the image capturing condition memory 84.

In case that a set of convexities and concavities or a bar code is not provided on the proximal end 44a of the compression plate 44, or in case that the radiographic image capturing apparatus 16 is devoid of the compression plate size detector 50, then the radiologist may operate the input operating unit 90 in order to manually enter information concerning the compression plate 44. The entered information concerning the compression plate 44 is stored in the image capturing condition memory 84. Further, even in case that a set of convexities and concavities or a bar code is provided on the proximal end 44a, and even in case that the radiographic image capturing apparatus 16 is equipped with the compression plate size detector 50, the radiologist can still operate the input operating unit 90 in order to enter information concerning the compression plate 44.

The controller 82 controls the display unit 92 in order to display the ID information, the image capturing method, and the image capturing conditions, which have been set, and information concerning the compression plate 44. The radiologist visually confirms the information that is displayed on the display unit 92. In case that necessary, the radiologist may operate the input operating unit 90 in order to manually enter additional information, or to change the displayed information.

The image capturing conditions, which are stored in the image capturing condition memory 84, are sent from the transceiver 80 to the transceiver 76 of the radiographic image capturing apparatus 16, whereupon the image capturing conditions are set in the radiation source controller 70.

As described later, the calibration image capturing process is carried out in step S2, and the breast image capturing process (pre-irradiating process) is carried out on the compressed breast 14 in step S6. In step S1, the image capturing conditions both for the calibration image capturing process and the breast image capturing process may be set in the radiation source controller 70. Alternatively, in step S1, the image capturing conditions for the calibration image capturing process may be set in the radiation source controller 70, and in step S6, the image capturing conditions for the breast image capturing process may be set in the radiation source controller 70.

In step S2, the radiologist operates the display control panel 74 (see FIG. 4) in order to actuate the compression plate moving mechanism 46, thereby lowering the compression plate 44 until the compression surface 52 of the compression plate 44 is brought into contact with the rest surface 38 of the image capturing table 36, as shown in FIG. 6. Thereafter, the radiologist operates the display control panel 74 or the input operating unit 90 in order to instruct the breast thickness measuring apparatus 10 to perform the calibration image capturing process. At this time, the radiation source controller 70 carries out the calibration image capturing process during which radiation 40 is emitted from the radiation source 28, which is placed in position A, toward the compression plate 44, according to the image capturing conditions for the calibration image capturing process that were set in step S1. FIG. 6 schematically illustrates the calibration image capturing process.

As shown in FIG. 6, the marker 54 is located within a range that is irradiated with radiation 40. Among the radiation 40 that is emitted from the radiation source 28 and which is applied to the compression plate 44, a portion of the radiation 40 is applied to and absorbed by the marker 54, whereas the remainder of the radiation 40 passes through the compression plate 44 and reaches the radiation detector 42.

The radiation detector 42 detects radiation 40 that has reached the radiation detector 42, and converts the radiation 40 into a radiographic image (first radiographic image, calibration image, projected image). Since the radiation 40 is partially absorbed by the marker 54, the marker 54 is projected as a marker image (first marker image) 100 within the radiographic image, at a location corresponding to the marker 54. Therefore, the marker image 100 is included within the radiographic image.

FIG. 6 shows schematically the detection surface 102 of the radiation detector 42 for detecting radiation 40 and converting the detected radiation 40 into a radiographic image. The detection surface 102 includes a pixel 104 for converting a portion of the radiation 40 into the marker image 100. FIG. 6 also schematically shows the marker image 100. In FIG. 6, the marker 54, which is irradiated with radiation 40, is shown as being projected onto the single pixel 104, and converted into the marker image 100 by the single pixel 104. According to the present embodiment, however, the marker 54 that is irradiated with radiation 40 may be projected onto a plurality of respective pixels 104, and converted into the marker image 100 by such pixels 104.

In step S3, the detector controller 72 acquires a radiographic image from the radiation detector 42, and sends the acquired radiographic image through the transceivers 76, 80 to the console 18. In a case where the radiographic image is received by the console 18, the controller 82 stores the received radiographic image in the image memory 86.

In step S4, the marker detector 94 reads the radiographic image that is stored in the image memory 86, and detects the marker image 100 included within the read radiographic image. Upon detecting the marker image 100, the marker detector 94 identifies, on the detection surface 102 of the radiation detector 42, the position of the marker image 100 within the radiographic image, i.e., the position of the pixel 104 onto which the marker 54, which is irradiated with radiation 40, is projected.

More specifically, on a Y-Z plane shown in FIG. 6, which is defined by the Y-axis and a Z-axis that extends in the direction of the arrow Z, the marker detector 94 identifies a distance Y1 (position of the first marker image) from the origin O to the pixel 104 where the first marker image 100 is positioned. In this case, the position immediately below the side surface of the holder 34 defines the origin O of the Y-axis and the Z-axis on the detection surface 102.

On the Y-Z plane shown in FIG. 6, the radiation source 28 has a focus 112, the coordinate position (the position of the radiation source 28) of which is represented by (Y0, Z0). Further, the distance from the surface (origin O) of the holder 34 to the side surface 62 of the compression plate 44 is represented by Yp (size of the compression plate 44), and the spacing between the rest surface 38 and the detection surface 102, i.e., the height of the rest surface 38 from the origin O, is represented by Zf.

In FIG. 6, the marker 54 is irradiated with radiation 40, and the marker 54 is projected onto the single pixel 104, which converts the marker 54 into the marker image 100. Further, in FIG. 6, to facilitate illustration, the coordinate position of the focus 112 is represented by (Y0, Z0), because the focus 112 is illustrated as lying on the Y-Z plane. However, in case that the X-axis also is taken into account, the coordinate position of the focus 112 actually is represented by (X0, Y0, Z0).

Since according to the image capturing conditions, the radiation source 28 emits radiation 40 from position A, the coordinate position (X0, Y0, Z0) is made up of preset values. The distance Y0 and the spacing Zf also have preset values.

In step S5 (first step), the radiologist operates the display control panel 74 so that the compression plate moving mechanism 46 displaces the compression plate 44 upwardly. At this time, the compression plate moving mechanism 46 continues to lift the compression plate 44 until the spacing between the rest surface 38 and the compression surface 52 becomes wide enough to allow the breast 14 to be placed between the compression plate 44 and the image capturing table 36.

Next, the radiologist positions the breast 14 of the subject 12 with respect to the radiographic image capturing apparatus 16. More specifically, the radiologist places the breast 14 on the rest surface 38 of the image capturing table 36, such that the chest wall 56 of the subject 12 is kept in contact with the side surface 58 of the image capturing table 36, and the breast 14, which is an object to be imaged, is bilaterally symmetrical with respect to the vertical axis 32 and the central line 60.

Then, the radiologist operates the display control panel 74 to instruct the compression plate moving mechanism 46 to move the compression plate 44 gradually toward the image capturing table 36. The breast 14 is compressed and held in a prescribed position between the image capturing table 36 and the compression plate 44.

At this time, as shown in FIGS. 1, 6, and 7, the breast 14 is placed on the rest surface 38 at a location proximate the side surface 58, whereas the compression plate 44 is supported in a cantilevered fashion on the holder 34 through the proximal end 44a. In a case where the compression plate 44 is lowered toward the rest surface 38, a portion of the compression plate 44 in the vicinity of the distal-end side surface 62 of the compression surface 52 compresses the breast 14 downwardly. As a result, as shown in FIG. 7, the compression plate 44 is tilted upwardly toward the chest wall 56 of the subject 12 at an angle θ from the direction of the arrow Y.

In other words, in a case where the breast 14, which is placed on the rest surface 38, is pressed flatwise against the rest surface 38 by the compression plate 44, the compression plate 44 is subjected to flexure due to the shape of the breast 14, and the compression plate 44 compresses the breast 14 in a state of flexure. As shown in FIG. 7, on the Y-Z plane, the compression plate 44 is tilted upwardly at the angle θ from the direction of the arrow Y. Actually, at this time, due to the shape of the breast 14, the compression plate 44 also is subjected to flexure in the direction of the arrow X.

In FIG. 7, the two-dot-and-dash lines, which serve to indicate the compression plate 44 that is kept in contact with the rest surface 38, illustrate the position of the compression plate 44 as it is positioned during the calibration image capturing process in step S2.

The two-dot-and-dash lines, which appear immediately below the compression plate 44 shown by the solid lines and extend in the direction of the arrow Y toward the chest wall 56, illustrate, in a case where the breast 14 is not on the rest surface 38, the position of the compression plate 44 after the compression plate 44 has been lifted to the height Z1 from the rest surface 38 in the direction of the arrow Z. Therefore, in a case where the compression plate 44 compresses the breast 14, the compression plate 44 is tilted upwardly through the angle θ from the position shown by the two-dot-and-dash lines and presses and holds the breast 14.

In step S6 (second step), the radiologist operates the input operating unit 90 in order to instruct the breast thickness measuring apparatus 10 to perform the breast image capturing process (pre-irradiating process). At this time, according to the image capturing conditions set for the breast image capturing process, the radiation source controller 70 carries out the breast image capturing process for emitting radiation 40 from the radiation source 28, which is placed in position A, through the compression plate 44 and toward the compressed breast 14.

At this time, the marker 54 also is located within the range that is irradiated with radiation 40. Among the radiation 40 that is emitted from the radiation source 28 and applied to the compression plate 44, a portion of the radiation 40 is applied to and absorbed by the marker 54, whereas the remainder of the radiation 40 is transmitted through the compression plate 44, or through both the compression plate 44 and the breast 14, whereupon the radiation 40 reaches the radiation detector 42.

The radiation detector 42 detects radiation 40 that has reached the radiation detector 42, and converts the detected radiation 40 into a radiographic image (second radiographic image, projected image). Since the radiation 40 is partially absorbed by the marker 54, the marker 54 is projected as a marker image (second marker image) 106 in the radiographic image at a location corresponding to the marker 54. Therefore, in the radiographic image, both the marker image 106 and the breast image representing the breast 14 are included. As described above, the marker 54 is placed in a position spaced a prescribed distance from the distal-end side surface 62 of the compression plate 44 that faces toward the chest wall 56. Since the marker 54 is disposed on the compression plate 44 in spaced-apart relation to the compressed breast 14, in the radiographic image, the marker image 106 is prevented from being included within the breast image.

In step S7 (third step), the detector controller 72 acquires the radiographic image from the radiation detector 42, and sends the acquired radiographic image through the transceivers 76, 80 to the console 18. Upon receipt of the radiographic image by the console 18, the controller 82 stores the received radiographic image in the image memory 86.

In step S8 (fourth step), the marker detector 94 reads the radiographic image stored in the image memory 86, and detects the marker image 106 that is included within the read radiographic image. In a case where the marker detector 94 detects the marker image 106, the marker detector 94 identifies the position of the marker image 106 in the radiographic image. More specifically, the marker detector 94 detects the position of a pixel 108, onto which the marker 54 that is irradiated with radiation 40 is projected, on the detection surface 102 of the radiation detector 42. In other words, on the Y-Z plane shown in FIG. 7, the marker detector 94 identifies a distance Y2 from the origin O to the pixel 108 where the second marker image 106 is positioned.

In FIG. 7, the marker 54 that is irradiated with radiation 40 is shown as being projected onto a single pixel 108, and the marker 54 is converted into the marker image 106 by the single pixel 108. According to the present embodiment, however, the marker 54 that is irradiated with radiation 40 may be projected onto a plurality of pixels 108, and converted into the marker image 106 by the plurality of pixels 108.

In FIG. 7, for illustrative purposes, the positions of the marker image 100 and the pixel 104 also are shown. It should be noted, however, that the marker image 100 and the pixel 104 are not involved in the breast image capturing process.

In FIG. 7, the height of the marker 54 from the detection surface 102 is represented by Z2, whereas the distance along the Z-axis by which the compression plate 44 is tilted at the time that the breast 14 is compressed, i.e., the height by which the compression plate 44 is tilted through the angle θ, is represented by Z3. The compressed thickness of the breast 14 at the chest wall 56, i.e., the distance along the direction of the arrow Z from the rest surface 38 on the chest wall 56 side to a corner 109 of the compression plate 44 where the compression surface 52 and the side surface 62 intersect each other, is represented by Zp. The height Z1 has a measured value, which is detected by the compression plate position detector 48.

In step S9, the compressed thickness calculator 96 calculates the vertical position (height Z2) of the marker 54 on the compression plate 44, which has compressed the breast 14 in the breast image capturing process of step S6.

Figure 8:
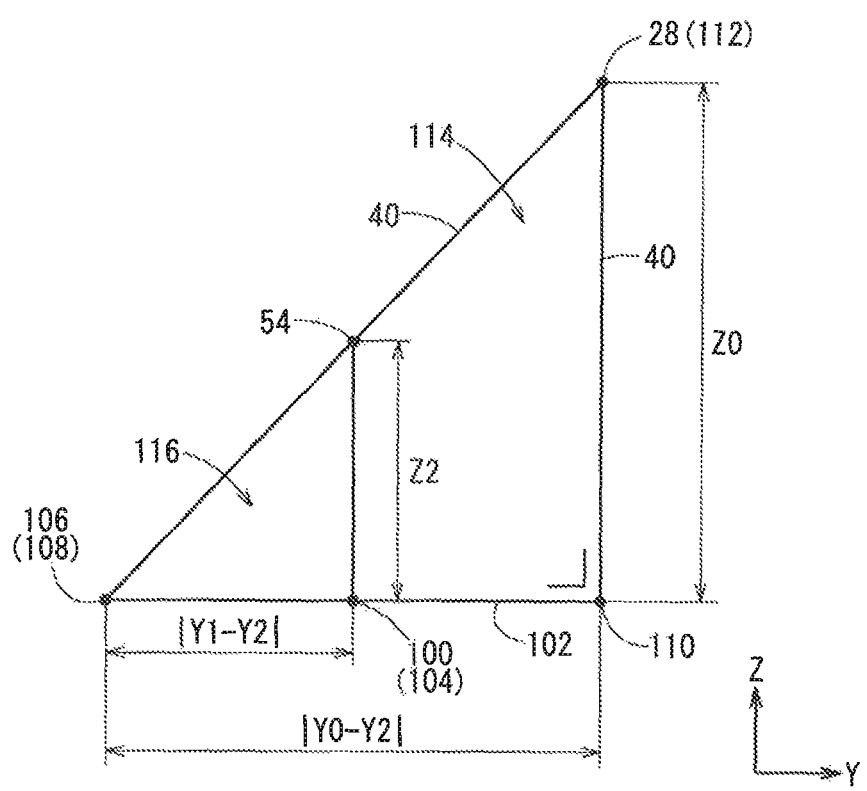
FIG. 8 is a diagram showing approximated components and dimensions for calculating a vertical position of a marker.

In FIG. 8, the components shown in FIG. 7 are represented approximately in the form of triangles 114, 116, for thereby calculating the height Z2 of the marker 54. In FIG. 8, the major components of the radiographic image capturing apparatus 16 shown in FIG. 7 are illustrated as vertices of the triangles 114, 116. In addition, the path of the radiation 40 and the detection surface 102 are illustrated schematically as sides of the triangles 114, 116. Reference numeral 110 denotes a position (projected position 110) at which the focus 112 of the radiation source 28 is projected onto the detection surface 102 along the direction of the arrow Z.

In FIG. 8, the triangle 114 is a right triangle, in which a leg serving as the vertical side representing a vertical path of the radiation 40, and a leg serving as a horizontal side representing the detection surface 102 form a 90° angle at the projected position 110. In case that the angle θ is small and the positions of the marker image 106 and the pixel 108 lie close to the origin O, then at the time the breast 14 is compressed, any positional shift of the marker 54 along the direction of the arrow Y is negligible.

Consequently, the marker image 100 and the pixel 104 can be regarded as being positioned approximately on the detection surface 102, directly below the marker 54 along the direction of the arrow Z. The distance from the origin O to the marker image 100 and the pixel 104 can be represented approximately by |Y1−Y2|.

The triangle 114 is a larger triangle, the vertices of which are represented by the marker image 106 (pixel 108), the projected position 110, and the focus 112 (radiation source 28). The triangle 116 is a smaller triangle, the vertices of which are represented by the marker image 106, the marker image 100 (pixel 104), and the marker 54. The triangles 114, 116 are of an approximately similar relationship to each other, i.e., are similar triangles.

As a result, on the basis of the similarity between the two triangles 114, 116, the height Z2 of the marker 54 at the time that the breast image capturing process is carried out on the breast 14, which is compressed by the compression plate 44 in step S6, is determined according to the following equations (1) and (2) from the relationship between the height Z0 and the distances Y0, Y1, Y2.

$$Z2:Z0=|Y1-Y2|:|Y0-Y2| \quad (1)$$

$$Z2=Z0\times|Y1-Y2|/|Y0-Y2| \quad (2)$$

In step S9, a case has been described in which the height Z2 of the marker 54 from the reference surface represented by the detection surface 102 is detected. On the other hand, in case that the rest surface 38 is used as the reference surface, then in view of the spacing Zf between the detection surface 102 and the rest surface 38, the height Z21 of the marker 54 is calculated from the following equation (3), which is a modification of equation (2).

$$Z21=Z2-Zf=Z0\times|Y1-Y2|/|Y0-Y2|-Zf \quad (3)$$

In step S10 (fifth step), the compressed thickness calculator 96 calculates the vertical position (height Zp) of the compression plate 44, which has compressed the breast 14 in the breast image capturing process of step S6.

Figure 9:
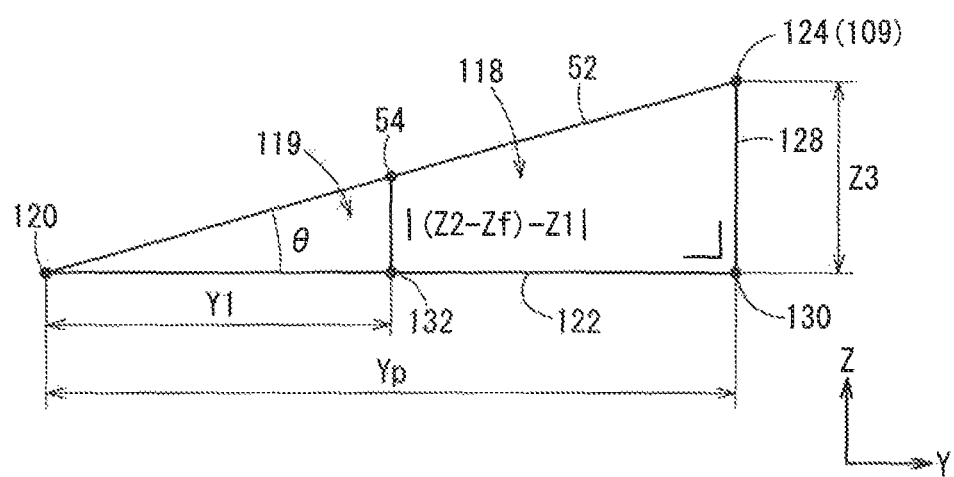
FIG. 9 is a diagram showing approximated components and dimensions for calculating a gradient of a the compression plate.

FIG. 9 shows approximated representations of the components shown in FIG. 7 in the form of triangles 118, 119, for thereby calculating the distance Z3 by which the compression plate 44 is tilted. In FIG. 8, the major components of the radiographic image capturing apparatus 16, which are shown in FIG. 7, are illustrated as vertices of the triangles 118, 119, and the compression surface 52, etc., are schematically illustrated as hypotenuses of the triangles 118, 119.

Assuming that the angle θ is small and the marker image 106 and the pixel 108 lie close to the origin O, the common vertex 120 of the triangles 118, 119 represents a point of intersection between the side surface (Z-axis) of the holder 34 and a straight line that extends from the compression surface 52. In addition, the length of the bottom side 122 of the triangle 118, which extends from the vertex 120 in the direction of the arrow Y, is regarded as the total length (distance Yp) along the direction of the arrow Y of the compression plate 44 that is indicated by the two-dot-and-dash lines.

The triangle 118 has a vertex 124 positioned at the corner 109 of the compression plate 44 near the chest wall 56. A point of intersection between the bottom side 122 and the vertical side 128 of the triangle 118, which extends from the vertex 124 along the direction of the arrow Z, serves as another vertex 130 of the triangle 118.

The triangle 118 is a right triangle, in which a leg serving as the bottom side 122 and a leg serving as the vertical side 128 form a 90° angle at the vertex 130. Since, as described above, the angle θ is small and the marker image 106 and the pixel 108 lie close to the origin O, at the time that the breast 14 is compressed, any positional shift of the marker 54 along the direction of the arrow Y is negligible.

Consequently, the marker image 100 and the pixel 104 can be regarded as being positioned approximately on the detection surface 102, directly below the marker 54 along the direction of the arrow Z. A point of intersection 132 on the bottom side 122 represents a projected position onto which the marker 54 is projected along the direction of the arrow Z, and a projected position onto which the marker image 100 and the pixel 104 are projected toward the bottom side 122 along the direction of the arrow Z.

The triangle 118 is a larger triangle, the vertices of which are represented by the vertex 120, the vertex 124 (corner 109), and the vertex 130. The triangle 119 is a smaller triangle, the vertices of which are represented by the vertex 120, the marker 54, and the point of intersection 132. The triangles 118, 119 are of an approximately similar relationship, i.e., are similar triangles.

The distance Z3 by which the compression plate 44 is tilted at the time that the breast image capturing process is carried out on the breast 14, which is compressed by the compression plate 44 in step S6, is determined according to the following equations (4) and (5), from the relationship between the heights Z1, Z2, the spacing Zf, and the distances Y1, Yp, and on the basis of the similarity between the two triangles 118, 119.

$$Z3:|(Z2-Zf)-Z1|=Yp:Y1 \quad (4)$$

$$Z3=|(Z2-Zf)-Z1|\times Yp/Y1 \quad (5)$$

Therefore, using the distance Z3 and the height Z1, the compressed thickness calculator 96 can determine the compressed thickness Zp of the breast 14 at a location near the chest wall 56, according to the following equation (6).

$$Zp=Z1+Z3 \quad (6)$$

In step S10, calculation of the distance Z3 from the reference surface, which is represented by the detection surface 102, has been described. On the other hand, in case that the rest surface 38 is used as a reference surface, the distance Z31 by which the compression plate 44 is tilted from the rest surface 38, and the compressed thickness Zp are calculated respectively from the following equations (7) and (8), which are modifications of equations (5) and (6).

$$Z31=|Z2-Z1|\times Yp/Y1 \quad (7)$$

$$Zp=Z1+Z31 \quad (8)$$

The above description applies for conditions in which the angle θ is small. Thus, the distances Z3, Z31, which correspond to the value of tan θ, can be expressed by the following equation (9).

$$Z3 \text{ or } Z31=\tan\theta\approx\theta \quad (9)$$

In step S10, an approximate value of the angle θ, which is the angle through which the compression plate 44 is tilted at the time that the breast 14 is compressed by the compression plate 44, is calculated approximately by determining the distances Z3, Z31. In other words, in step S10, on the assumption that the angle θ is small, the distances Z3, Z31 may be determined approximately as the angle θ, rather than the value of tan θ.

In step S10, as described above, the distances Z3, Z31 are determined by regarding the length of the bottom side 122 to be Yp. However, inasmuch as the angle θ is small, the distances Z3, Z31 may be determined approximately by regarding the length of the hypotenuse (compression surface 52) of the triangle 118 shown in FIG. 9 to be Yp.

In step S11, after the compressed thickness Zp has been calculated, the controller 82 controls the display unit 92 in order to display various information items, including the compressed thickness Zp calculated by the compressed thickness calculator 96. In step S12, the controller 82 controls the image processor 88 in order to process the radiographic image that was stored in the image memory 86, and thereafter, the controller 82 controls the display unit 92 in order to display the processed radiographic image. The controller 82 may control the display unit 92 so as to display the processed radiographic image and the compressed thickness Zp simultaneously.

Thereafter, the radiographic image capturing system 20 sets, based on the compressed thickness Zp, image capturing conditions for a main image capturing process (radiographic image capturing process), and carries out the main image capturing process on the compressed breast 14 according to the set image capturing conditions. Consequently, a radiographic image of the breast 14, which is of good image quality, is acquired.

Figure 10A:
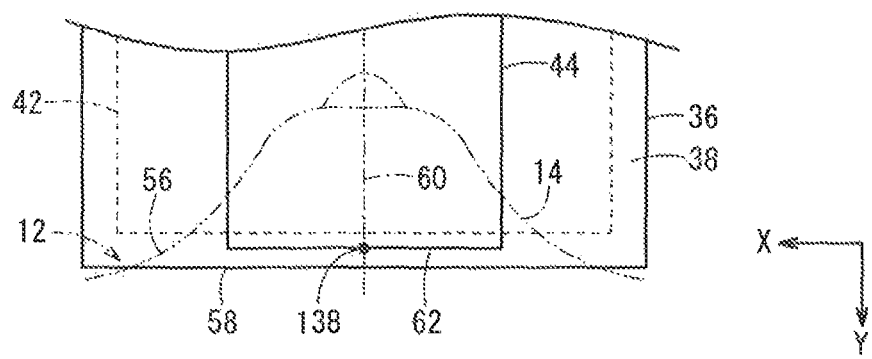
FIGS. 10A through 10C are plan views showing in plan a plurality of positions for determining a compressed breast thickness.
Figure 10B:
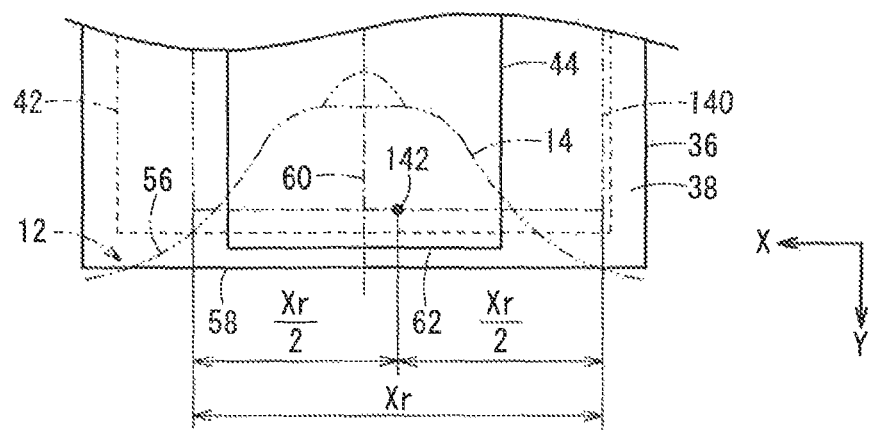
Figure 10C:
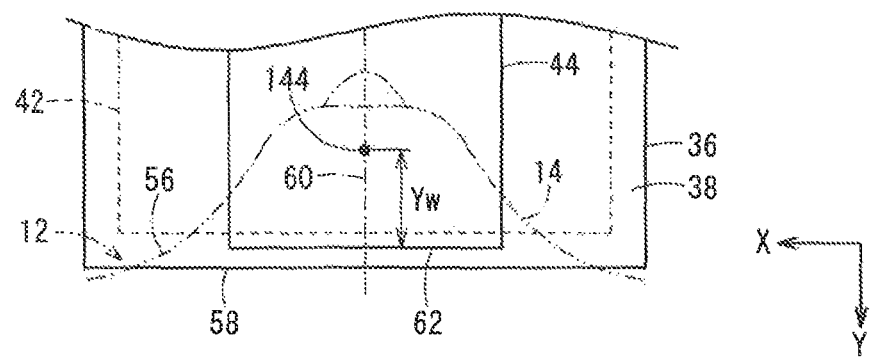

FIGS. 10A through 10C show in plan view positions that are used for determining the compressed thickness Zp. As has been described above, and as shown in FIG. 10A, the compressed thickness Zp is determined at a position 138 in plan on the central line 60 at the side surface 62.

According to the present embodiment, the position at which the compressed thickness Zp is determined is not limited to the position 138 shown in FIG. 10A. Alternatively, as shown in FIG. 10B, in case that an irradiated field 140 of radiation 40 covers a portion of the radiation detector 42, given that the irradiated field 140 has a width Xr along the direction of the arrow X, the compressed thickness Zp may be determined at a central position 142 (midpoint of the width Xr) of the irradiated field 140 at the side surface 62.

Alternatively, as shown in FIG. 10C, the compressed thickness Zp may be determined at a position 144, which in plan view is spaced a distance of Yw from the side surface 62 toward the proximal end 44a (see FIGS. 1, 2, 6, and 7) along the central line 60.

As described above, the position of the marker image 100 is detected in step S4, and the position of the marker image 106 is detected in step S8. According to the present embodiment, however, step S4 may be dispensed with, and the positions of the marker images 100, 106 may both be detected in step S8.

Further, as described above, in step S12, the radiographic image is displayed on the display unit 92. However, according to the present embodiment, since at the time of step S8, the radiographic image that is captured by the calibration image capturing process and the radiographic image that is captured by the breast image capturing process are both stored in the image memory 86, the display process of step S12 for displaying the radiographic image may be carried out at any time subsequent to step S8.

As described above, in preparation for the breast image capturing process, the calibration image capturing process is carried out in step S2, before the breast 14 is compressed in step S5. Further, according to the present embodiment, since the calibration image capturing process may be carried out and the position of the marker image 100 may be detected before the breast 14 is compressed, the principles of the present invention can also be applied to the following examples.

Upon installation of the radiographic image capturing apparatus 16 or the radiographic image capturing system 20, the calibration image capturing process is carried out once, the position of the marker image 100 is detected in steps S2 through S4, and the detected position of the marker image 100 is stored in the image capturing condition memory 84.

Alternatively, the calibration image capturing process is carried out periodically, the position of the marker image 100 is detected in steps S2 through S4, and the detected position of the marker image 100 is stored in the image capturing condition memory 84.

Consequently, in either of the above examples, steps S2 through S4 of FIG. 5 are dispensed with, and steps S1 and S5 through S12 are carried out in the subsequent breast image capturing process. In this case, in step S1, the compression plate size detector 50 reads the bar code, which is provided on the proximal end 44a of the compression plate 44, and acquires information concerning the compression plate 44. Based on the acquired information, in case that it is determined that the compression plate 44 is the same as the compression plate 44 used during the calibration image capturing process, the position of the marker image 100, which is stored in the image capturing condition memory 84, can be used in the processing sequence that is carried out from step S9.

In step S12, the image processor 88 may perform a marker removal correction process, so as to remove the marker image 100 from the radiographic image and generate a radiographic image of the breast 14 that is free of the marker 54, and the generated radiographic image may be displayed on the display unit 92. Further, the marker removal correction process may correct the pixel data of the marker image 100 using pixel data in the vicinity of the marker image 100, for example. The image processor 88 may simultaneously display the radiographic image, which is generated by the marker removal correction process, together with the measured compressed thickness Zp (breast thickness) on the display unit 92.

Advantages of the Present Embodiment

As described above, the breast thickness measuring apparatus 10 according to the present embodiment detects the marker images 100, 106, which are included within the radiographic image, and calculates the thickness of the compressed breast 14 (compressed thickness Zp) on the basis of the positions of the detected marker images 100, 106, the position (focus 112) of the radiation source 28, and information concerning the compression plate 44. More specifically, the breast thickness measuring apparatus 10 calculates the compressed thickness Zp using a single radiographic image, which is produced by a single breast image capturing process (pre-irradiating process) performed on the breast 14, and a single calibration image capturing process performed while the breast 14 is not irradiated with radiation 40.

In other words, according to the present embodiment, the compressed thickness Zp can be calculated without the need for a plurality of radiographic image capturing processes to be performed on the breast 14, as disclosed in Japanese Laid-Open Patent Publication No. 2006-280444. Thus, the compressed thickness Zp can accurately be determined without requiring the subject 12 to be exposed to an unduly high dose of radiation.

Image capturing conditions for a main image capturing process are set on the basis of the compressed thickness Zp, which is obtained from the radiographic images acquired by the pre-irradiating process and the calibration image capturing process. Thereafter, the main image capturing process is performed on the compressed breast 14 according to the image capturing conditions that have been set. As a result, a radiographic image of the compressed breast 14, which is of good image quality, can reliably be acquired.

The compressed thickness calculator 96 calculates the compressed thickness Zp on the basis of the positions of the marker images 100, 106 (distances Y1, Y2), the position of the focus 112 of the radiation source 28 (distances Y0, Z0), the position of the compression plate 44 that compresses the breast 14 (height Z1), and the size of the compression plate 44 (distance Yp). Thus, the compressed thickness Zp is calculated with high accuracy using the position and size of the compression plate 44, as represented by the information concerning the compression plate 44.

According to the present embodiment, as indicated by the flowchart shown in FIG. 5, only the marker image 100 is detected from the radiographic image that is produced by the calibration image capturing process (step S4), and the marker image 106 is detected from the radiographic image that is produced by the next breast image capturing process (step S8).

Therefore, the compressed thickness calculator 96 can calculate the position of the marker 54 (height Z2) on the compression plate 44, which compresses the breast 14, from the positions of the detected marker images 100, 106, etc. In addition, the compressed thickness calculator 96 can calculate the distance Z3 by which the compression plate 44, which compresses the breast 14, is tilted from the heights Z1, Z2, etc. Accordingly, even though the compression plate 44 undergoes flexure due to the shape of the breast 14 at the time that the breast 14 is pressed flatwise against the image capturing table 36, the distance Z3 by which the compression plate 44 is tilted can accurately be calculated while taking into account the flexure of the compression plate 44.

Therefore, even though the tilted compression plate 44 compresses the breast 14, the compressed thickness calculator 96 can accurately calculate the compressed thickness Zp of the breast 14, on the basis of the height Z1 of the compression plate 44 and the distance Z3 by which the compression plate 44 is tilted.

Since the marker 54 is disposed at a position that is spaced a prescribed distance from the side surface 62 of the compression plate 44 near the chest wall 56, and preferably is positioned more deeply in the compression plate 44 in such a manner that the marker images 100, 106 are included within the radiographic images at positions spaced from the chest wall 56 and the breast 14 of the subject 12, the marker images 100, 106 are prevented from being included within the breast image.

According to the present embodiment, the compressed thickness Zp of the compressed breast 14 is determined using the similarity between the triangles 114, 116, 118, 119 on the Y-Z plane. Therefore, the present embodiment can be applied not only to a process for capturing a radiographic image with the radiation source 28 arranged in position A (CC mammogram), but also to a process for capturing a radiographic image with the radiation source 28 arranged in position B or position C. In other words, the present embodiment is applicable to a tomosynthetic process for capturing a radiographic image while the arm 26 is turned within an angular range from $-\alpha 1$ to $+\alpha 1$, i.e., an angular range between position B and position C. The present embodiment can also be applied in order to perform a biopsy of the breast 14.

For capturing an MLO mammogram, the arm 26, the holder 34, and the image capturing table 36 are turned in unison around the rotatable shaft 24, and hence, the XYZ coordinate system of the radiographic image capturing apparatus 16 also is turned in unison therewith. Consequently, assuming that the rest surface 38 of the image capturing table 36 lies in the X-Y plane, and the arm 26 and the holder 34 extend in the direction of the arrow Z, the present embodiment may also be applied to a process for capturing an MLO mammogram.

Modification of the Embodiment

A modification of the breast thickness measuring apparatus 10 according to the present embodiment will be described below with reference to FIGS. 11 and 12.

Figure 11:
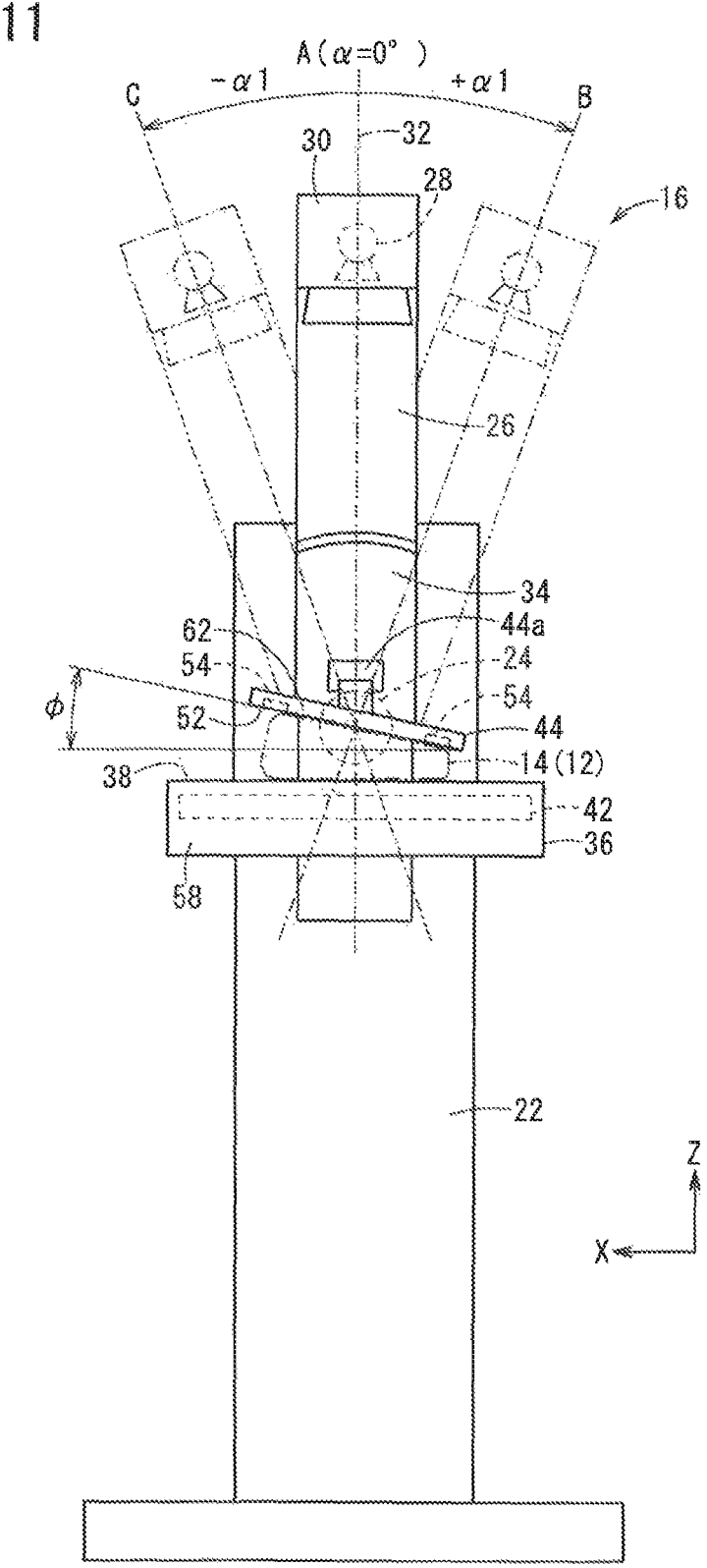
FIG. 11 is a front elevational view of a modification of the breast thickness measuring apparatus shown in FIG. 1.
Figure 12:
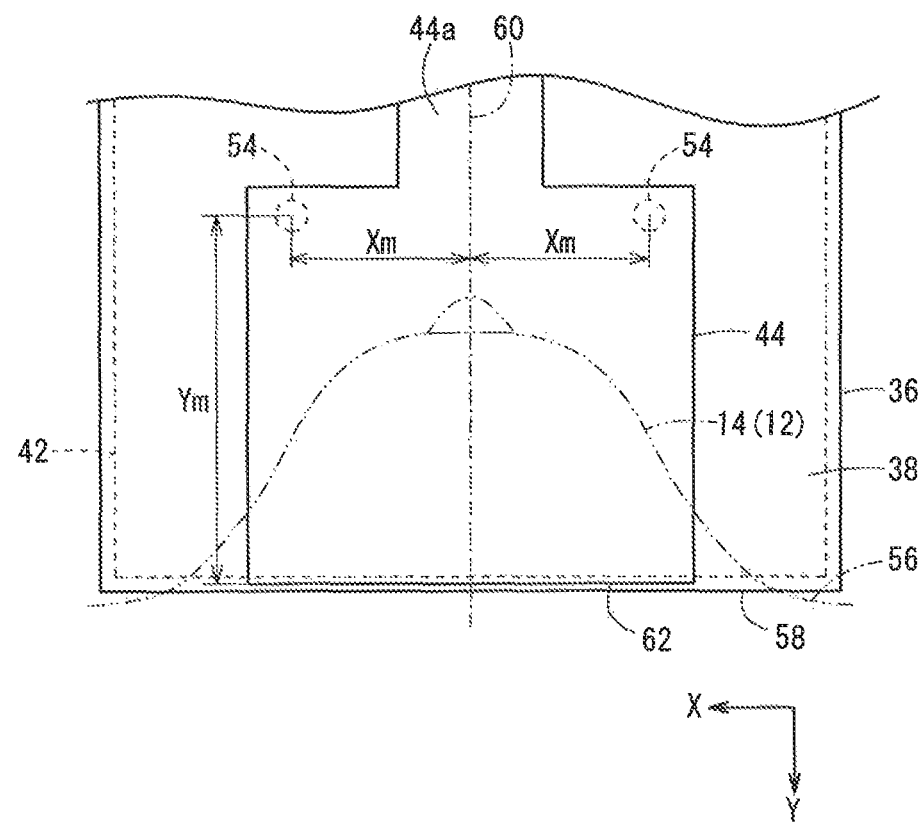
FIG. 12 is a plan view of a compression plate and a support table of the radiographic image capturing apparatus, according to the modification shown in FIG. 11.

According to the modification, as shown in FIGS. 11 and 12, two markers 54, which are spaced from each other along the direction of the arrow X, are disposed on the compression plate 44 near the proximal end 44a of the compression plate 44.

As shown in FIG. 12, the markers 54 are positioned one on each side of the central line 60 of the compression plate 44. Each of the markers 54 is spaced a distance Xm from the central line 60 along a direction perpendicular to the central line, i.e., the direction of the arrow X. Each of the markers 54 also is spaced a distance Ym from the side surface 62 toward the proximal end 44a. Each of the markers 54 is embedded in the compression plate 44, such that the lower surface thereof lies substantially flush with the compression surface 52 of the compression plate 44. Consequently, according to the modification, the markers 54 are not positioned on the central line 60. Furthermore, the two markers 54 are spaced by the distance Ym from the side surface 62 of the compression plate 44 near the chest wall 56 of the subject 12 as viewed in plan. As shown in FIG. 12, the two markers 54 are positioned more closely to a side surface of the compression plate 44, which is opposite to the side surface 62, than to the side surface 62 on the chest wall 56 side, and the markers 54 are positioned more closely to the lateral sides of the compression plate 44 than to the central line 60. As illustrated in FIG. 12, the two markers 54 are positioned symmetrically with respect to the central line 60. According to the modification, however, the two markers 54 may be positioned asymmetrically with respect to the central line 60 of the compression plate 44.

Under a condition in which the breast 14 is compressed by the compression plate 44, as described above, the compression plate 44 is subjected to flexure, i.e., becomes tilted, in the direction of the arrow Y. At the same time, as shown in FIG. 11, the compression plate 44 tends to become tilted laterally in the direction of the arrow X shown in FIG. 11. In this case, in case that the compression plate 44 is tilted laterally through an angle $\varphi$, it is necessary to calculate the thickness of the breast 14 while also taking into consideration the lateral tilt of the compression plate 44.

According to the present modification, a correction process, to be described below, is carried out in order to accurately calculate the compressed thickness Zp, while taking into account the angle $\varphi$ through which the compression plate 44 is tilted laterally.

The compressed thickness calculator 96 calculates the heights Z2 (Z21) of the two markers 54. The tilt-angle calculator 98 determines the angle $\varphi$ according to the following equations (10) and (11), from the height difference $\Delta Z2$ ($\Delta Z21$) between the heights Z2 (Z21) of the two markers 54 along the direction of the arrow Z, and the distance $\Delta X$ between the two markers 54 along the direction of the arrow X.

$$\varphi = \tan^{-1}(\Delta Z2/\Delta X) \quad (10)$$

$$\varphi = \tan^{-1}(\Delta Z21/\Delta X) \quad (11)$$

The compressed thickness calculator 96 calculates the compressed thickness Zp according to equations (5) through (9) while also taking into account the angle $\varphi$ calculated by the tilt-angle calculator 98. Therefore, even in case that the compression plate 44 is tilted laterally with respect to the image capturing table 36 at the time that the compression plate 44 compresses the breast 14, the compressed thickness calculator 96 can suitably calculate the compressed thickness Zp.

In particular, during a process of capturing an MLO mammogram, in a case where the breast 14 is displaced to the right or left along the direction of the arrow X on the rest surface 38, and is compressed by the compression plate 44, the compression plate 44 is tilted laterally. At this time, by determining the angle $\varphi$, the compressed thickness Zp can be calculated accurately. According to the modification, it also is possible to determine the compressed thickness Zp at the positions 138, 144 as viewed in plan, and the central position 142 shown in FIGS. 10A through 10C.

Further, according to the modification, the compressed thickness calculator 96 calculates the compressed thickness Zp while also taking into account the angle φ. Therefore, the function of the tilt-angle calculator 98 may be included in the compressed thickness calculator 96.

Although a preferred embodiment of the present invention has been described above, it should be understood that various changes and modifications may be made to the embodiment without departing from the scope of the invention as set forth in the appended claims.

What is claimed is:

1. A breast thickness measuring apparatus comprising:
    a support table on which a breast of a subject is placed;
    a compression plate configured to compress the breast, which is placed on the support table;
    a marker disposed on the compression plate;
    a radiation source configured to apply radiation in a prescribed direction to the breast, which is compressed by the compression plate;
    a radiographic image generator configured to generate a radiographic image based on radiation that has passed through the breast;
    a marker detector configured to detect, from the radiographic image, a marker image representing the marker included within the radiographic image;
    a thickness calculator configured to calculate a thickness of the breast, which is compressed, from a position of the detected marker image, a position of the radiation source, and information concerning the compression plate;
    a compression plate position detector configured to detect a position of the compression plate; and
    a compression plate size acquirer configured to acquire a size of the compression plate,
    wherein the thickness calculator calculates the thickness of the breast, which is compressed, based on the position of the detected marker image, the position of the radiation source, the position of the compression plate, which compresses the breast, and the size of the compression plate.

2. The breast thickness measuring apparatus according to claim 1, wherein:
    the radiographic image generator generates a first radiographic image based on the radiation, which is applied from the radiation source through the compression plate while the compression plate is held in contact with the support table, and generates a second radiographic image based on the radiation, which is applied from the radiation source through the compression plate, and has passed through the breast while the compression plate compresses the breast;
    the marker detector detects a first marker image, which is included within the first radiographic image, and a second marker image, which is included within the second radiographic image; and
    the thickness calculator calculates the position of the marker on the compression plate, which compresses the breast, based on the position of the first marker image, the position of the second marker image, and the position of the radiation source, calculates the distance by which the compression plate, which compresses the breast, is tilted, based on the calculated position of the marker, the calculated position of the first marker image, the position of the compression plate, which compresses the breast, and the size of the compression plate, and calculates the thickness of the breast, which is compressed, based on the position of the compression plate, which compresses the breast, and the calculated distance by which the compression plate, which compresses the breast, is tilted.

3. The breast thickness measuring apparatus according to claim 1, wherein the marker is disposed in a position spaced a prescribed distance from a side surface of the compression plate, the side surface closest to a chest wall of the subject.

4. The breast thickness measuring apparatus according to claim 1, wherein:
    the marker comprises a plurality of respective markers that are positioned one on each side of a central line of the compression plate;
    the marker detector detects marker images representing the plurality of respective markers included within the radiographic image; and
    the thickness calculator calculates an angle through which the compression plate, which compresses the breast, is tilted laterally, based on respective positions of the detected marker images, and calculates the thickness of the breast, which is compressed, based on the calculated angle through which the compression plate, which compresses the breast, is tilted laterally, the positions of the marker images, the position of the radiation source, and the information concerning the compression plate.

5. A breast thickness measuring method comprising:
    a first step of causing a compression plate having a marker disposed thereon to compress a breast of a subject that is placed on a support table;
    a second step of causing a radiation source to apply radiation in a prescribed direction to the breast, which is compressed by the compression plate;
    a third step of causing a radiographic image generator to generate a radiographic image based on radiation that has passed through the breast;
    a fourth step of causing a marker detector to detect, from the radiographic image, a marker image representing the marker included within the radiographic image;
    a fifth step of causing a thickness calculator to calculate a thickness of the breast, which is compressed, from a position of the detected marker image, a position of the radiation source, and information concerning the compression plate;
    a sixth step of detecting a position of the compression plate; and
    a seventh step of acquiring a size of the compression plate,
    wherein the fifth step of causing the thickness calculator to calculate the thickness of the breast comprises causing the thickness calculator to calculate the thickness of the breast, which is compressed, based on the position of the detected marker image, the position of the radiation source, the position of the compression plate, which compresses the breast, and the size of the compression plate.

6. A radiographic image capturing system comprising:
    a support table on which a breast of a subject is placed;
    a compression plate configured to compress the breast, which is placed on the support table;
    a marker disposed on the compression plate;
    a radiation source configured to apply radiation in a prescribed direction to the breast, which is compressed by the compression plate;

a radiographic image generator configured to generate a radiographic image based on radiation that has passed through the breast;
a marker detector configured to detect, from the radiographic image, a marker image representing the marker included within the radiographic image;
a thickness calculator configured to calculate a thickness of the breast, which is compressed, from a position of the detected marker image, a position of the radiation source, and information concerning the compression plate;
a display unit configured to display the radiographic image and the calculated thickness of the breast;
a compression plate position detector configured to detect a position of the compression plate; and
a compression plate size acquirer configured to acquire a size of the compression plate,
wherein the thickness calculator calculates the thickness of the breast, which is compressed, based on the position of the detected marker image, the position of the radiation source, the position of the compression plate, which compresses the breast, and the size of the compression plate.

7. A breast thickness measuring apparatus comprising:
a support table on which a breast of a subject is placed;
a compression plate configured to compress the breast, which is placed on the support table;
a marker disposed on the compression plate;
a radiation source configured to apply radiation in a prescribed direction to the breast, which is compressed by the compression plate;
a radiographic image generator configured to generate a radiographic image based on radiation that has passed through the breast;
a marker detector configured to detect, from the radiographic image, a marker image representing the marker included within the radiographic image; and
a thickness calculator configured to calculate a thickness of the breast, which is compressed, from a position of the detected marker image, a position of the radiation source, and information concerning the compression plate,
wherein the marker comprises a plurality of respective markers that are positioned one on each side of a central line of the compression plate;
wherein the marker detector detects marker images representing the plurality of respective markers included within the radiographic image; and
wherein the thickness calculator calculates an angle through which the compression plate, which compresses the breast, is tilted laterally, based on respective positions of the detected marker images, and calculates the thickness of the breast, which is compressed, based on the calculated angle through which the compression plate, which compresses the breast, is tilted laterally, the positions of the marker images, the position of the radiation source, and the information concerning the compression plate.

8. A breast thickness measuring method comprising:
a first step of causing a compression plate having a marker disposed thereon to compress a breast of a subject that is placed on a support table;
a second step of causing a radiation source to apply radiation in a prescribed direction to the breast, which is compressed by the compression plate;
a third step of causing a radiographic image generator to generate a radiographic image based on radiation that has passed through the breast;
a fourth step of causing a marker detector to detect, from the radiographic image, a marker image representing the marker included within the radiographic image; and
a fifth step of causing a thickness calculator to calculate a thickness of the breast, which is compressed, from a position of the detected marker image, a position of the radiation source, and information concerning the compression plate,
wherein the marker comprises a plurality of respective markers that are positioned one on each side of a central line of the compression plate;
wherein the fourth step of causing the marker detector to detect, from the radiographic image, the marker image representing the marker included within the radiographic image comprises causing the marker detector to detect marker images representing the plurality of respective markers included within the radiographic image; and
wherein the fifth step of causing the thickness calculator to calculate the thickness of the breast comprises causing the thickness calculator to calculate an angle through which the compression plate, which compresses the breast, is tilted laterally, based on respective positions of the detected marker images, and to calculate the thickness of the breast, which is compressed, based on the calculated angle through which the compression plate, which compresses the breast, is tilted laterally, the positions of the marker images, the position of the radiation source, and the information concerning the compression plate.

9. A radiographic image capturing system comprising:
a support table on which a breast of a subject is placed;
a compression plate configured to compress the breast, which is placed on the support table;
a marker disposed on the compression plate;
a radiation source configured to apply radiation in a prescribed direction to the breast, which is compressed by the compression plate;
a radiographic image generator configured to generate a radiographic image based on radiation that has passed through the breast;
a marker detector configured to detect, from the radiographic image, a marker image representing the marker included within the radiographic image;
a thickness calculator configured to calculate a thickness of the breast, which is compressed, from a position of the detected marker image, a position of the radiation source, and information concerning the compression plate; and
a display unit configured to display the radiographic image and the calculated thickness of the breast,
wherein the marker comprises a plurality of respective markers that are positioned one on each side of a central line of the compression plate;
wherein the marker detector detects marker images representing the plurality of respective markers included within the radiographic image; and
wherein the thickness calculator calculates an angle through which the compression plate, which compresses the breast, is tilted laterally, based on respective positions of the detected marker images, and calculates the thickness of the breast, which is compressed, based on the calculated angle through which the compression plate, which compresses the breast, is tilted laterally, the positions of the marker images, the position of the radiation source, and the information concerning the compression plate.

* * * * *